US006383753B1

(12) United States Patent
Thiele et al.

(10) Patent No.: US 6,383,753 B1
(45) Date of Patent: May 7, 2002

(54) YEAST MAMMALIAN REGULATORS OF CELL PROLIFERATION

(75) Inventors: Dennis J. Thiele; Phillip C. C. Liu, both of Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/540,824

(22) Filed: Mar. 31, 2000

Related U.S. Application Data
(60) Provisional application No. 60/127,226, filed on Mar. 31, 1999.

(51) Int. Cl.[7] .......................... C12Q 1/68; C12P 21/06; C07H 19/00
(52) U.S. Cl. .......................... 435/6; 435/69.1; 536/22.1
(58) Field of Search .............................. 435/6, 4, 91.1, 435/252.3, 255.1, 255.2, 69.1; 536/22.1, 23.1

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,965,188 A | 10/1990 | Mullis et al. | 435/6 |

OTHER PUBLICATIONS

Johnston M et al. The nucleotide sequence of *Saccharomyces cerevisae* chromosome XII. Nature, 387 (6632 suppl): 87–90, 1997.*

Ansari–Lari MA et al. Large–scale sequencing in human chromosome 12p 13: experimental and computational gene structure determination. Genome Res., 7(3): 268–280, 1997.*

Sinha, et al., "Polymer support oligonucleotide synthesis XVIII: use of beta–cyanoethyl–N,N–dialkyl-amino–/N–morpholino phosphoramidite of deoxynucleosides for the synthesis of DNA fragments simplifying deprotection and isolation of the final product," *Nucleic Acids Research*, 12:4539–4557 (1984).

Rout, et al., "The yeast nuclear pore complex: composition, architecture and transport mechanism," *J Cell Biol*, 148:635–651 (2000).

Hakuno, et al., "The *Scizosaccharomyces pombe mral* gene, which is required for cell growth and mating, can suppress the mating inefficiency caused by a deficit in the Ras 1 activity" *Genes to Cells* 1:303–315 (1996).

* cited by examiner

*Primary Examiner*—Jeffrey Fredman
*Assistant Examiner*—Suryaprabha Chunduru
(74) *Attorney, Agent, or Firm*—Medlen & Carroll, LLP

(57) ABSTRACT

Novel, highly conserved cell cycle regulatory genes (Emg1 and ENIP1) are described along with methods employing Emg1 and ENIP1 to detect compounds that are agonistic or antagonistic to cell cycle progression.

4 Claims, 22 Drawing Sheets

Alignment of yeast Emg1p with other eukaryotic homologues

```
  1  M - - - - - - - - - - - - - - - - - - - - - - - - - - - - - - - - - - - - - - - - -  S.cerev.
  1  M P T Y S K R K S R G S L E V S E K T N Q P K F I K R S Q S S E T I T S G E T A       S.pombe
  1  M S - - - - - - - - - - - - - - - - - - - - - - - - - - - - - - - - - - - - - - - -  C.elegans
  1  M S A - - - - - A S G G F - - - - - - Q P R - - - - - - - - - - - - - - - - - - - -  mouse
  1  - - - - - - - - - - - D G F - - - - - - K P R - - - - - - - - - - - - - - - - - - -  human 2  - - - - - - - - - - - - - - V E D S - - - R V R D A - - - - - - - - - - - - - - - -  S.cerev.
 41  S E L M Q D E K E Q S N G A V G S I E D E E L Q R L R E N Q A S V E A L S K K P       S.pombe
  3  - - - - - - - - - - - - - - - - - - - - - - - - - - - - - - - - - - - - - - - - - -  C.elegans
 12  - - - - - - - - - - - - - - - - - - - - - - - - - - - - - - - - - - - - - - - - - -  mouse
  7  - - - - - - - - - - - - - - - - - - - - - - - - - - - - - - - - - - - - - - - - - -  human 11  - - - - - - - - - - - - - - L K G G D Q K - - - - - - - - - - - - - - - A L          S.cerev.
 81  E S I D R E L G V E A L E I D N V V K S D E E K E D P N G A S S K T V K A R P L       S.pombe
  3  - - - - - - - - - - - - - - - H E Y D - - - - - - - - - - - - - - - - - - T V        C.elegans
 12  - - - E R F S V Q E D E - - - - - - - - - - - - - - - - - - - - - - - - - T T        mouse
  7  - - - E R S G E Q D D - - - - - - - - - - - - - - - - - - - - - - - - - - A L        human 20  P A S - - - - - - - L V P Q A P P V L T S K D K I K M V V L A M S L E                 S.cerev.
121  P A G S V H V T T H M A P I P A R S I G S H D T T Q R L V V L D Q A C L E             S.pombe
  9  A P N A K R M K T - - - - - - - - - - D N Q L E D K K I L V V L E G C S L E           C.elegans
 26  - P P K L R L G A - - - - - - - - - - G S K C G G R R - L I V V L E G A S L E         mouse
 21  - P P K R P R L G A - - - - - - - - - G N K I G G R R - L I V V L E G A S L E         human 52  H R I S S N G P G G D K V L L K C D D H Q G L L K M G R D I S E A R P D I             S.cerev.
161  I Y K V G K - - A K D A K Y Q L L N C D D H Q G L L K K L N R N I A Q A R P D I       S.pombe
 39  A K V G G E - - - - - - Y A I L S S D K H A N F L R K Q K K P A D Y R P D I           C.elegans
 54  T V K V G K - - - - - - Y E L L K C D R H K S M L L K G K D P G E V R P D I           mouse
 49  T V K V G K T - - - - - Y E L L K C D K H K S I L L K N G R D P G E A R P D I         human 92  T H Q C L L T L L D S P I K A G K L Q V Y I Q T S R G I L I E V K P T V K P           S.cerev.
199  T H Q C L L T L L D S P L K A G R L Q V Y I H T A R K V L I E V K P S V R I P         S.pombe
 73  L H Q C L L N L L D S P L K A G K L R V F F R T S K N V L V D V S P Q C R I P         C.elegans
 88  T H Q S L L M L M D S P L N R A G L L Q V Y I H T Q K N V L I E V K P Q T R I P       mouse
 83  T H Q S L L M L M D S P L N R A G L L Q V Y I H T Q R N V L I E V K P Q T R I P       human 132  R K K R S G L K V Q L L H L L S I R S V N S E E K L L K V I K N P I T D R L           S.cerev.
239  R T P K R F S G L K V Q L L H L L S I R S V N G N E K L L K V I K N P T T D Y L       S.pombe
113  R T P L R F C G L K V Q L L H L S I R A E T T K K L M S V K N P V S N L L             C.elegans
128  R T F D R F C G L K V Q L L H L S V R A A D G P Q K L L K V I K N P V S D H F         mouse
123  R T F D R F C G L K V Q L L H K L S V R A A D G P Q K L L K V I K N P V S D H F       human 172  F T K D K L T S F D A F I R V Q D Y I E K D D D E S I C V F G A M L R                 S.cerev.
279  P P N C R A T L S F D P T P P P R K Y E T L Q P N Q S C I A I G M H                   S.pombe
153  P V G S R M L M S F N V E L T M A N K L A P E T D E L L I I G I R                     C.elegans
168  P V G M I T S F V E D I S I V P S S - - D P V F V V G A H                              mouse
163  P V G M K G T S F I V S D V R L V P S S - - D P I F V V G A H                          human 212  G D N F A D L D R V G L S L P S A S V A C S R F C H G A E D A N                       S.cerev.
319  G P D D F S D G W V D F I S - S D Y P L S A S I A C S K F L H S M E D F L G           S.pombe
193  G - - I V D N S E T K I S K Y P L S A A L T C A K V S G L E I G I                     C.elegans
206  G K - - V S V E Y T E K M V S I S K Y P L S A A L T C A K V T A F E E V G V            mouse
201  G K - - V S V E Y T E K M V S I S N Y P L S A A L T C A K L T T A F E E V G V          human 252  L                                                                                     S.cerev.
359  V                                                                                     S.pombe
231  I                                                                                     C.elegans
244  I                                                                                     mouse
239  I                                                                                     human
```

Figure 2

Complementation of *emg1*Δ cells by the mouse Emg1 homologue mEmg1 Genomic Structure Expression in Mouse Tissues

Figure 5

Human EMG1 cDNA sequence and encoded protein

```
1/1                                           31/11
gat gga ttc aag cct cgt gaa cga agc ggt ggg gag cag gca cag gac tgg gat gct ctg
 D   G   F   K   P   R   E   R   S   G   G   E   Q   A   Q   D   W   D   A   L
61/21                                         91/31
cca ccc aag cgg ccc cga cta ggg gca gga aac aag atc gga ggc cgt agg ctt att gtg
 P   P   K   R   P   R   L   G   A   G   N   K   I   G   G   R   R   L   I   V
121/41                                        151/51
gtg ctg gaa ggg gcc agt ctg gag aca gtc aag gta ggg aag aca tat gag cta ctc aac
 V   L   E   G   A   S   L   E   T   V   K   V   G   K   T   Y   E   L   L   N
181/61                                        211/71
tgt gac aag cac aag tct ata ttg ttg aag aat gga cgg gac cct ggg gaa gcg cgg cca
 C   D   K   H   K   S   I   L   L   K   N   G   R   D   P   G   E   A   R   P
241/81                                        271/91
gat atc acc cac cag agt ttg ctg atg ctg atg gat agt ccc ctg aac cga gct ggc ttg
 D   I   T   H   Q   S   L   L   M   L   M   D   S   P   L   N   R   A   G   L
301/101                                       331/111
cta cag gtt tat atc cat aca cag aag aat gtt ctg att gaa gtg aat ccc cag acc cga
 L   Q   V   Y   I   H   T   Q   K   N   V   L   I   E   V   N   P   Q   T   R
361/121                                       391/131
att ccc aga acc ttt gac cgc ttt tgt ggc ctc atg gtt caa ctt tta cac aag ctc agt
 I   P   R   T   F   D   R   F   C   G   L   M   V   Q   L   L   H   K   L   S
421/141                                       451/151
gtt cga gca gct gat ggc ccc cag aag ctt ttg aag gta att aag aat cca gta tca gat
 V   R   A   A   D   G   P   Q   K   L   L   K   V   I   K   N   P   V   S   D
481/161                                       511/171
cac ttt cca gtt gga tgt atg aaa gtt ggc act tct ttt tcc atc ccg gtt gtc agt gat
 H   F   P   V   G   C   M   K   V   G   T   S   F   S   I   P   V   V   S   D
541/181                                       571/191
gtg cgt gag ctg gtg ccc agc agt gat cct att gtt ttt gtg gta ggg gcc ttt gcc cat
 V   R   E   L   V   P   S   S   D   P   I   V   F   V   V   G   A   F   A   H
601/201                                       631/211
ggc aag gtc agt gtg gag tat aca gag aag atg gtg tcc atc agt aac tac ccc ctt tct
 G   K   V   S   V   E   Y   T   E   K   M   V   S   I   S   N   Y   P   L   S
661/221                                       691/231
gct gcc ctc acc tgt gca aaa ctt acc aca gcc ttt gag gaa gta tgg ggg gtc att tga
 A   A   L   T   C   A   K   L   T   T   A   F   E   E   V   W   G   V   I   *
```

Figure 6

S.cerevisiae EMG1 coding region sequence and encoded protein

```
  1 ATG GTC GAA GAT TCC AGA GTT AGA GAC GCC CTC AAA GGT GGT GAT CAG AAG GCA TTA CCG   60
  1  M   V   E   D   S   R   V   R   D   A   L   K   G   G   D   Q   K   A   L   P    20

61 GCC TCT TTG GTT CCT CAA GCA CCT CCT GTC TTG ACA TCA AAG GAT AAG ATT ACT AAG CGG  120
 21  A   S   L   V   P   Q   A   P   P   V   L   T   S   K   D   K   I   T   K   R    40

121 ATG ATT GTG GTA TTA GCG ATG GCA TCC CTC GAG ACA CAC AAG ATA TCG TCC AAC GGG CCT  180
 41  M   I   V   V   L   A   M   A   S   L   E   T   H   K   I   S   S   N   G   P    60

181 GGT GGT GAC AAA TAT GTC CTT TTG AAC TGT GAC GAC CAT CAA GGT TTA TTA AAA AAA ATG  240
 61  G   G   D   K   Y   V   L   L   N   C   D   D   H   Q   G   L   L   K   K   M    80

241 GGT AGA GAC ATT AGT GAA GCA AGA CCT GAT ATT ACC CAC CAA TGT CTT TTG ACG TTG CTA  300
 81  G   R   D   I   S   E   A   R   P   D   I   T   H   Q   C   L   L   T   L   L   100

301 GAT TCT CCA ATC AAC AAA GCC GGA AAG CTG CAG GTC TAT ATT CAA ACA AGT CGA GGA ATT  360
101  D   S   P   I   N   K   A   G   K   L   Q   V   Y   I   Q   T   S   R   G   I   120

361 CTG ATC GAG GTT AAC CCC ACT GTT CGT ATA CCA AGA ACT TTC AAA AGA TTT TCA GGT TTA  420
121  L   I   E   V   N   P   T   V   R   I   P   R   T   F   K   R   F   S   G   L   140

421 ATG GTT CAG TTA CTA CAT AAG CTT TCT ATC AGA TCG GTA AAT TCT GAA GAA AAG TTA CTT  480
141  M   V   Q   L   L   H   K   L   S   I   R   S   V   N   S   E   E   K   L   L   160

481 AAA GTC ATT AAG AAC CCA ATT ACC GAT CAC CTA CCT ACT AAG TGC CGT AAG GTG ACA TTA  540
161  K   V   I   K   N   P   I   T   D   H   L   P   T   K   C   R   K   V   T   L   180

541 TCC TTT GAC GCA CCA GTT ATC CGC GTT CAA GAT TAC ATC GAA AAA CTA GAC GAT GAT GAA  600
181  S   F   D   A   P   V   I   R   V   Q   D   Y   I   E   K   L   D   D   D   E   200

601 AGT ATA TGT GTC TTT GTT GGT GCC ATG GCA AGA GGT AAA GAT AAC TTT GCG GAT GAA TAC  660
201  S   I   C   V   F   V   G   A   M   A   R   G   K   D   N   F   A   D   E   Y   220

661 GTC GAC GAA AAA GTC GGC TTG TCC AAT TAC CCA TTG TCT GCC TCA GTT GCA TGT TCT AAA  720
221  V   D   E   K   V   G   L   S   N   Y   P   L   S   A   S   V   A   C   S   K   240

721 TTT TGC CAT GGC GCT GAA GAT GCT TGG AAT ATT TTA TAG                              759
241  F   C   H   G   A   E   D   A   W   N   I   L   *                              253
```

Mouse EMG1 cDNA sequence and encoded protein

```
  1 ATG TCT GCG GCC AGT GGT GGC TTC CAA CCT CGT GAG CGG CGA TTT TCA GTG CAG GAG CAG  60
  1  M   S   A   A   S   G   G   F   Q   P   R   E   R   R   F   S   V   Q   E   Q   20

61 GAC TGG GAG ACT ACG CCG CCT AAG AAG CTC CGG CTT GGG GCA GGA AGC AAG TGC GGA GGC 120
 21  D   W   E   T   T   P   P   K   K   L   R   L   G   A   G   S   K   C   G   G   40

121 CGG AGG CTC ATT GTG GTG CTG GAA GGG GCC AGT CTG GAG ACA GTC AAG GTA GGG AAA ACT 180
 41  R   R   L   I   V   V   L   E   G   A   S   L   E   T   V   K   V   G   K   T   60

181 TAC GAG CTA CTC AAC TGT GAC AGG CAC AAG TCC ATG TTG TTG AAG AAT GGA CGG GAC CCA 240
 61  Y   E   L   L   N   C   D   R   H   K   S   M   L   L   K   N   G   R   D   P   80

241 GGG GAA GTC AGA CCA GAC ATC ACC CAC CAG AGC CTG CTG ATG CTT ATG GAC AGC CCC CTG 300
 81  G   E   V   R   P   D   I   T   H   Q   S   L   L   M   L   M   D   S   P   L  100

301 AAC CGA GCT GGC TTG CTA CAG GTT TAC ATC CAC ACA CAG AAG AAC GTG CTG ATT GAA GTG 360
101  N   R   A   G   L   L   Q   V   Y   I   H   T   Q   K   N   V   L   I   E   V  120

361 AAC CCC CAG ACT CGA ATT CCT AGA ACC TTT GAC CGA TTT TGT GGC CTC ATG GTT CAG CTT 420
121  N   P   Q   T   R   I   P   R   T   F   D   R   F   C   G   L   M   V   Q   L  140

421 TTA CAC AAA CTG AGC GTC CGA GCA GCC GAC GGC CCT CAG AAG CTA TTG AAG GTA ATT AAG 480
141  L   H   K   L   S   V   R   A   A   D   G   P   Q   K   L   L   K   V   I   K  160

481 AAT CCA GTG TCC GAC CAC TTC CCA GTT GGC TGT ATG AAA ATT GGC ACT TCC TTT TCT GTT 540
161  N   P   V   S   D   H   F   P   V   G   C   M   K   I   G   T   S   F   S   V  180

541 GAA GAC ATC AGT GAC ATT CGA GAG TTG GTG CCC AGT AGT GAC CCA GTT GTG TTT GTG GTG 600
181  E   D   I   S   D   I   R   E   L   V   P   S   S   D   P   V   V   F   V   V  200

601 GGG GCC TTT GCC CAT GGC AAG GTC AGT GTG GAG TAC ACA GAA AAG ATG GTG TCC ATC AGC 660
201  G   A   F   A   H   G   K   V   S   V   E   Y   T   E   K   M   V   S   I   S  220

661 AAC TAT CCA CTC TCT GCT GCG CTT ACC TGT GCT AAA GTC ACC ACA GCT TTT GAA GAA GTA 720
221  N   Y   P   L   S   A   A   L   T   C   A   K   V   T   T   A   F   E   E   V  240

721 TGG GGT GTC ATT tga                                                              735
241  W   G   V   I                                                                  244
```

Figure 7

SEQUENCES FOR PROBES cga att ccc aga acc ttt gac cgc ttt  (SEQ ID NO:12)

cga att ccc aga acc ttt gac cgc  (SEQ ID NO:13)

att ccc aga acc ttt gac  (SEQ ID NO:14)

att ccc aga acc ttt  (SEQ ID NO:15)

```
  1 AATAATTCGGAATTGTTTTAACCATATACAACTACTTTTACGAT ATG GGC GGT CAG GGC AAG GCG ATC AAT AGG AAG CGT AAG          85
  1                                                  M   G   G   Q   G   K   A   I   N   R   K   R   K        13

86 TTT GTC GGT CGC AAG GCG GAC GAT CCG GAG TTC GAT CTG GAC AAG AAG CAA TTC AAG GTG CTC CAT CTG AAT GCC      160
 14  F   V   G   R   K   A   D   D   P   E   F   D   L   D   K   K   Q   F   K   V   L   H   L   N   A       38

161 ACC GAA AAG CGG CTG ATC ATC GTT TTG GAA GGA GCC CAA CTG GAG ACG GTG AAG CAC AAC ACT TTC AAG CTG          235
 39  T   E   K   R   L   I   I   V   L   E   G   A   Q   L   E   T   V   K   H   N   T   F   K   L           63

236 CTG AAC TGC GAC GAT CAC GCG GGA ATT ATG CGC AAA AAC CAA AGA GAT CCC GGT TCC TGC CGT TCG GAC ATC ACC      310
 64  L   N   C   D   D   H   A   G   I   M   R   K   N   Q   R   D   P   G   S   C   R   S   D   I   T       88

311 CAC CAA TGC CTG TTG ATG CTC TTT GAT TCG CCA AAC CTG CTT CAG ACA TTT AAA CGC TTT GCT GTC TTT GTG          385
 89  H   Q   C   L   L   M   L   F   D   S   P   N   L   L   Q   T   F   K   R   F   A   V   F   V          113

386 CAT AAT GTG CTT ATC GAA ATC AAT CCC CAG ACG CGC ATC CCG AGG ACA TTT AAA CGC TTT GCT GGC CTA ATG GTG      460
114  H   N   V   L   I   E   I   N   P   Q   T   R   I   P   R   T   F   K   R   F   A   G   L   M   V      138

461 CAA TTG CTG CAC AAG TTC CAA ATT CGC GCC AAT GAC TCC TCA CGT CGT CTG ATG AGT GTC ATT AAG AAT CCG ATT      535
139  Q   L   L   H   K   F   Q   I   R   A   N   D   S   S   R   R   L   M   S   V   I   K   N   P   I      163

536 ACG GAT CAT GTG CCG GTC CAT GTC TGC AAA TAC AAG AAG TAC GCC ATG AGC TTC TCT GGC AAA CTA TTG CCC AAT      610
164  T   D   H   V   P   V   H   V   C   K   Y   K   K   Y   A   M   S   F   S   G   K   L   L   P   N      188

611 CTG GTG CCA CAT GGT GAC GAG ACG TCG GCC AGC TAT GAT GAG CCG GTG GTC ATC GTT ATT GGA GCC TTC GCA CAT      685
189  L   V   P   H   G   D   E   T   S   A   S   Y   D   E   P   V   V   I   V   I   G   A   F   A   H      213

686 GGC GTT CTC AAA ACG GAC TAC ACG GAG GAG CTG TTC TCC ATT AGC CTT TCG GCG GCC ATC GCG TGC                  760
214  G   V   L   K   T   D   Y   T   E   E   L   F   S   I   S   L   S   A   A   I   A   C                  238

761 TCC AAA ATC TGT TCC GCC TTC GAG GAG GTT TGG GGC GTG GTA TAA                                              805
239  S   K   I   C   S   A   F   E   E   V   W   G   V   V   *                                              253
```

Mutations in *emg1-1*

Ile104Ser
Lys109Pro

|  |  | S.cerev. | SEQ ID NO:18 |
|--|--|----------|--------------|
|  |  | S.pombe | SEQ ID NO:19 |
|  |  | C.elegans | SEQ ID NO:20 |
|  |  | mouse | SEQ ID NO:21 |
|  |  | human | SEQ ID NO:22 |

Nucleic Acid Sequence of human ENIP (Open Reading Frame)

```
CCTGTCTCTCTTCGGGTCTCGGGCCCTTGGGCGCCAGGCGGCGCCATGGCGAAGGCGAAGAAGGTCGGGGCGAA
GGAAGGCCTCCGGGGCGCCGGCGGGGAGCGCGGAGGGGCCCGGCGAAGGCCAACTCCAATCCGTTCGAGGTGAAAGTTAAC
AGGCAGAAGTTCCAGATCCTGGGCCGGAAGACGCGCCACGACGTGGGACTGCCCGGGTGTCTCGCGCACGGGCCCTCAG
GAAGCGTACACCAGACTTTACTAAAGAGTACAAAGAAAGGGATAAATCCAATGTATTCAGAGATAAACGCTTCGGAGAAT
ACAACAGCAACATGAGCCCCGAGGAGAAGATGAAGAATTGACTCATTATGCCAGTCTTTGCAGACATCGAGAAGCATAATGACATTGT
ATCTACAATCTAAATGAAGATGAAGAATTGACTCATTATGCCAGTCTTTGCAGACATCGAGAAGCATAATGACATTGT
GGACAGTGACAGCGATGCTGAGGATCGAGGAACGTTGTCTGCTGAGCTGACTGTGCCCACTTTGGAGGAGGCGGTGGGC
TCCTTCACAAGAAGACTCAACGAGAAGGCCGAGGAGGCGGGAGAAACCGAAGTCCCGGAAAAGAGCTGATTGAAGAGCTCATT
GCCAAGTCAAAACAAGACTTCCTGTCCCACAAACTCCCAAGTCAGAAGCTCAACGAGAAGATGCCCTCGAGCTCACGGAGAAGCTAGACCAAGA
CTGGAAAGAAATTCAGACTCTCGTGCGAGCTTGGTTCGCGAGCTTGGCTTTGAAATGAAGGCGCAGCCTCTAACAGGATGAAGACGGAGGCAGAA
ATGCATATGACATGATGGTTCGCAGGACAGGAGCACCTCAGGAAGCTGAGCTGAATGATGGCTTCGTGCTAGATAAGATGACAGGCGTTTGC
TTGGCAAAGGAAGGAGAGCAGGAGCACCTCAGGAAGCTGAGCTGAATGATGGCTTCGTGCTAGATAAGATGACAGGCGTTTGC
AAATGTTAAGAAACCAAAACATATGTCGAGGAAGATGTCCAGGAGGAGACAGCCCAGATAGCCACTTGGACCTGAATC
TTTCCTACAAAGATGGAAAGATGAATGTCGAGGAAGATGTCCAGGAGGAGACAGCCCAGATAGCCACTTGGACCTGAATC
AACGTGGAGAGTGAGGAAGAAAACGAGAAGAGCAGCTGCCCTACACGTTCGCAGCCCCTGAATCCTATGAGGAAACTGAGATCT
CAACGTGGAGAGTGAGGAAGAAAACGAGAAGAGCAGCTGCCCTACACGTTCGCAGCCCCTGAATCCTATGAGGAAACTGAGATCT
AGGAGAGAGCTGGAAGATCGATGGAAGAACGCTTTTGGCTTTCTTTTGCACTTATATCATCTTTGCCAGATGTTCCTGAATCGCAAGTGACGCTATC
CTGTTGTTAGGAAGATCGATGGAAGAACGCTTTTGGCTTTCTTTTGCACTTATATCATCTTTGCCAGATGTTCCTGAATCGCAAGTGACGCTATC
AGGAAACAAAGCAAAATTAGAAAAACTGTTTGTGCACTTATATCATCTTTGCCAGATGTTCCTGAATCGCAAGTGACGCTATC
ACCTCACAGTCATTGATAAGTTGGTTGTGCAGATCATGAACTTCGCTATTCCAACTTCCGTCCTCCTGAGACGTGGTAAGGCCTGTTCGTGTCTGCCTG
AAATTTGTTCTCCGAGATGCGATCGATGCATGAGATGCATGAGATGAAGAAATGATTGAGAACAAGACCCAGTGGTGACCCCTGCCCTCG
TGTGCTCATTTATTTGAAAATCACTGGGCTGCTATTCCAACTTCCGTCCTCCTGAGACGTGGTAAGGCCTGTTCGTGTCTGCCTG
TGTGCTCAGTCAGCTGCTCACCAAGTGCCCATCCTGTCCCAGAGGTTTATACCTGAGCTTATTAATTTCTTCTTGGATTCTTTACATAGCAAC
TTCCTGGAGTATGTGGCTTTGTCCCAGAGGTTTATACCTGAGCTTATTAATTTCTTCTTGGATTCTTTACATAGCAAC
TCCAAACAAGCAAGCCAAGGTTCCACTCTGGCAGAGCAGCCTTCCCTGCCCTTCAGAGCGCTTGGGAGAACTGGAACTGCTCGTGGTGT
CTGCTAGAGAGGCCAATCCTCCACGTGGCCACGTGGCCAGAGCAGCCTTCCCTGCCCTCGCTGGGCGAGTAGACTGAGGGCCCCAACTTCG
ACAGAGGCCAATCCTCCACGTGGCCACGTGGCCAGAGCAGCCTTCCCTGCCCTCGCTGGGCGAGTAGACTGAGGGCCCCAACTTCG
CCTGCCATCCTTCCACGCATCATGGGCCACTGACGAAGCAGACAGCTCTGCCGGCCCGTGACCTGTGAGAAG
AGCTCCAGAGCTGTGTCAGAGCACTGACCGAAGCAGACAGCTCTGCCGGCCCGTGACCTGTGAGAAG
AGCAAGCCTGTCCCACTGAAGCTTTTCACACCCGGCTGGTCAAGTCCTGGAGTTTGGAAGAAAACAAGGCAGTAGTAA
GGAGGAAACAGGAAAAGGAAGAGGCTGATCCACAAACAAGCGTGAATTTAAAGGGGCCGTTGAGAAATCGCAAGGACA
ATCAGTTCCTGGCGAGGATGCAACTCTCAGAAATCATGAACGGGATGCGAAAGAAAGCGGAAAGTAAAGCATTTTT
AACAGCCTGGCTACACAGGAAGGCGAATGGAAGGCTCTGAAGAGGAAAAAAGTTCAAAAATAA
```

Nucleic Acid Sequence of yENIP (Open Reading Frame)

```
ATGGCCGGTTCACAACTTAAGAATTTAAAGGCCGCCCTTGAAGGCCCGTGGACTCACAGTCAAACAAACGTCAAAAGTAA
GAATAAAAGAATTCCAAAGACAAGCGAAGGAGTATGATCGTGAAGAAAAAAAAAGGCCATTGCTGAAATCAGAGAAG
AGTTTAATCCGTTTGAAATAAAGGCTGCAAGGAGTAAGAGAGGAGAACAAAGAAAAGGCTGCCTTCTAAAACTGCTGATCGTATTGCT
GTGGGTAAGCCTGGTGTGATGTCTAAACAGATCGGTGAAGAACAAGCGTGCATTTGAAGCAAGAAAAATGTTGAAGAA
TAAACGTGGTGGTGTCGATAAGAGATTTGGTGAAAGAGACAAGTTGTTGACGGAAGAGACAAGTGAAGACGATGAAGACGACGGTGACATG
TCACCAGAGAAAGACAAAGCCAATCAAAGAGAAACGCAAATTTATTCAATCTTGAAGACGATGAAGACGACGGTGACATG
TTTGGAGACGGTCTTACACATTTAGTTCAATCGCTGTCCCTAGAAGATGAGCTTGCCAATGATGAAGCTTGAAGAGGA
TTCCAAACGATTCAATGAAGATGCTGAGCTACGACAAGAAGACAAAAGGCTCAAGTATATGAAGATCAAATAGATAATCTGAT
TCATTGCCAAATCAAAATTTTACAAACAAGAAGACAAAAGCTCAAGTATATGAAGATCAAATAGATAATCTGAT
GATAATTTCGAGGATGTTATGTCTGAATTGATGATGACGCAACCCAAGAAGAATCAATGGAACCTAAGACCGATCTAGA
TAAGGAGTATGATATCAAAGTGAAGAAACTACAATTGGACAAAAGAGCTGCACCCTCTGATAGAACTAAACTGAAGAGG
AGAAAAACGCTGAAGCTGAAGAAGAGGAGTTGGATGGAGATTCTGGGAAAATGAAGACTATGAAGACGATAATGA
GAAGAAGGCGAAGAAAGAGGAGTAGAGATATCAAATTGAAGATGGTTATTAGAAGACTATGAAGACGATAATGA
CGGTATTGCTGATTCTGATGATGATCATGCCCTAGAACTCATGATGCGTTATTAGAAACTCAAGTAAAAAATTAGACTTAGATGATCATCCT
AGAACATTTGTAAGAATATTATCAAGCTTACCAACCAAAATTGGCTGAAGTAATAAGGAAAAGTTAGGAAAATTCACCGC
TGTTTACTGACACATCAATTCATTTTCTAAGCAACTACCTAAACATCAAAACTACCTTAAACGTTCAAAGTTTTAAACGTACACAAATG
CATTGATCTCAATTCTAAAATCCCTTTCAGAGAAATATAATAGAGAGCTTTCCGAGAGTGTAGAGATTATATCAATGAA
ATGCAAGCACGCTATAAAGAACCATTTGAATGCTCTATCAAATGGTGATCGTGATTTTAATGAGCCAGTTCCTGAACAATCAAGT
TTTCTCCACCTCGGACCAGTACCATTTAGTAATAACTCCAGCATTGATTTAAGGATTGTTTCACAATATCAACGCATTCCAAACGGTAC
TTAATTCTTTAAAGAGGATAGCTTTTGGGCGTCGTCTTGGTAAGGATTGTTTCACAATATCAACGCATTCCAAACGGTAC
ATACCGGAGGTGGTTTACTTCTTTCAAAAATATTACTCACTTTTATAGTTGAGAAGAAATCAAGAAAAACCATTAGA
TTTGAAATATTACATACCTTGTCAACAATGGATACCGAGTTGGGCTTCCATTGGACGTTGACTTACAAAAAGAGATCAACTATTA
TTCCATTACATACCTTGTCAACAATGGATACCGAGTTGGGCTTCCATTGGACGTTGACTTACAAAAAGAGATCAACTATTA
GAATCTTTAGATGCAACTATCTCTACTGTGTGAAGAGCTTACCTGCTTCAATGAAATATTTTACCGATTCAGCAGTT
ATTAAGTGCATAACATATTCCGTTGGCTTTACAGAACCACAACCGTATCCATACCTACGCATGCTCCTAAATACGAAGAAAAC
TCACAGAACATATTCCGTTGGCTTTACAGAACCACAACCGTATCCATACCTACGCATGCTCCTAAATACGAAGAAAAC
TCAATCCTGATAAAAATCGTACGATCCTGATAGAACAAGAAGTGAGATAAATAAGATGAAGGCCCAACTAAGAAGGA
ACGTAAATTCACTATGAAGATAAAGAAATCCGTAAAGACGCCAAATTTGAAGCTAGACAAAGAATTGAAGAAAAGAACAAGGAGA
GCAGCGACTACCATGCAAAGATGCTCAATATTGTTAACACTATTAATAACCGAAGAAGGTGCGGAAAAAAACAAGTATGAA
AGAGAAAGAAACTACGTGGCGGAAGAAATAA
```

Figure 13

```
  1 MA--GSQLKNLKAALKARGLTGQTNVKSKNKKNSKRQAKE      S.c. ENIP    SEQ ID NO:25
  1 MGKNGSQLKNLKSSIRQANLGT---RPNNKKSRTRSTES       S.p. ENIP    SEQ ID NO:26
  1 MGV-------------------DKKQKQRK---             C.e. ENIP    SEQ ID NO:27
  1 LSLFGS----------RALGRSGARAMAKAKKVGARRKASG     H.s. ENIP    SEQ ID NO:28

39 YDREEKKKAIAEIREEFNPFEIKAARNK-RRDGLPSKTAD      S.c. ENIP
 37 ---HEDRQAKVQKIQSDFNLFDRQFTKRKFDVGGRRVKGTE     S.p. ENIP
 12 ----------------TNPFELKFNKSKHDILGRKK----      C.e. ENIP
 32 APAGARGGPA---KANSNPFEVKVNRQKFQILGRKT----      H.s. ENIP

78 RIAVGKPGISKQIGEEQRKRAFEARKMMKNKRGGVIDKRF      S.c. ENIP
 75 ----GKPGVSRGVGEELRRRTIGAELKKRNRSGAIIDRRF      S.p. ENIP
 32 GAQVGAPTASRKRAHEQREQTLGVEYDRKNKISKIVDKRL      C.e. ENIP
 65 RHDVGLPGVSRARALRKRTQTLLKEYKERDKSNVFRDKRF      H.s. ENIP

118 GERDKLLTEEEKMLERFTRERQSQSKRNANLFNL-----E      S.c. ENIP
111 GENNPHLSVEEKMLERFSREQQRRSKRE--LYNL-----D      S.p. ENIP
 72 GE-KDGKSEEEKGAMRFTEERVKNYKRASK-FNLTDDGDE      C.e. ENIP
105 GEYNSNMSPEEKMMKRFALEQRHHEKKSI-YNLNEDEE-       H.s. ENIP

153 DDE---DDGDMFGD--GLTHLGQSLSLEDE----LANDEE      S.c. ENIP
144 AEDVLTHGNRPLSDIDSFEEPGFGLDEGEE----LNDEVV      S.p. ENIP
110 EEEVLTHKGKALSDIEKYDKSMISDSDDDEEPGNLGSNMV      C.e. ENIP
143 ----LTHYGQSLADIEKHNDIVDSDSDA-EDRGTLSAELT      H.s. ENIP

184 DFLASKR---PNEDDAELQQPQR--KKTKAEVMKEVIAKS      S.c. ENIP
180 RRMHFGG---FEDSDAENEKEGEGAHKSKREVMSEIIAKS      S.p. ENIP
150 KVAHFGGE-----KTAEE-HVREKI-SREDMISNLIAKT      C.e. ENIP
178 -AAHFGGGGGLLHKKTQQEGEEREKPKSRKELIEELIAKS      H.s. ENIP

219 KFYKQERQKAQGIMEDQIDNLDDNFEDV---MSELMMTQP      S.c. ENIP
217 KHYKAERQAEKERYEDEREKLDEQMEDLQSFLSDYKKASR      S.p. ENIP
183 KLARHEKQQQKDELELMTESLDSKY---QALMGKMKASFR      C.e. ENIP
217 KQEKREROAQREDALELTEKLDQDWKEIQTLLSHKTP--K      H.s. ENIP

256 KKNPMEPK---TDLDKEYDIKVELQLDK--RAAPSDRTK      S.c. ENIP
257 KSGIKTQRPIISDGDARYDSFVREMVFDK--RAHPTERTK      S.p. ENIP
220 PTG---RQPLEK---DDYDKLTITLKTEADARATPADRKL      C.e. ENIP
255 SEN---RDKKEKPKPDAYDMMVRELGFEM--KAQPSNRMK      H.s. ENIP

291 TEEEKNAEAEEKKRELEQQRLDRMN--------GMIEL        S.c. ENIP
295 TEELAQIEADRLRELEDQRISRMEHYQEDSASEAGSIED       S.p. ENIP
254 SEEEALKEKERLETLEAAP------DADVDIDAGSKAD        C.e. ENIP
290 TEAELAKEEQEHLRKLEAERLRRMLGKDEDENVKKPKHMS      H.s. ENIP

321 EEGEE------RG------------------VE             S.c. ENIP
335 EQATDNVFGFGKG------------------LE             S.p. ENIP
287 ARKVQA-----KNSRFEVKFDDEGGLIDEDTVEKSRILKK      C.e. ENIP
330 ADDLNDGFVLDKDDRRLLSYKDGKMNVEEDVQEEQSKEAS      H.s. ENIP

330 DLDDGFWENEEDYEDDNDGIADSDDDIKFED---------      S.c. ENIP
350 QENEEEWNGINEEAESESDEESVNSDTSPVD---------      S.p. ENIP
322 NLDGSDESDDDEDLEDEEE--------DLDDLLEDEDELE      C.e. ENIP
370 DPESNEEEGDSSGGEDTEESDSPDSHLDLESNVESEEENE      H.s. ENIP

361 ---QGRDEGFSQILKKKNI------------SISCPRTHD      S.c. ENIP
381 ---DEQLKVEEQPLVGSAIKNEGSEKASLAYTYPCPTSHV      S.p. ENIP
354 EDSDDEEAQEAQKVVKKAKKSAPEPAETLPFVFEMPKNYK      C.e. ENIP
410 KPAKEQRQTPGKGLISGKERAGKATRDELPYTFAAPESYE      H.s. ENIP

386 ALLDQVKKLDLDDHPKIVKNIIKAYQPKLAEGNKEKLGKF      S.c  ENIP
418 EFVQLLKGLDYKDYPTVVSRIRTLHVKLHPDKKSRLENF       S.p. ENIP
394 KF-CALLEKHSESMDLVLERLVKCHPSLKEGNKKRLNKL       C.e  ENIP
450 ELRSLLLGRSMEEQLLVVERIQKCNHPSLAEGNKAKLEKL      H.s. ENIP
```

FIGURE 14A

```
426 T A V L L R H I I F L S N Q N Y L K N V Q S F K R T Q N A L I S I L K S L S E K    S.c. ENIP
458 S V I L L Q H I L H L T R Q P - M I S M E L L E H - - - - L T E H L H S L A Q Q    S.p. ENIP
433 F L L C L R W F D D M S K E E - L T A E S V K E M - - - - N L A Q - - - - - - -    C.e. ENIP
490 F G F L L E Y V G D L A T D D - P P D L T V I D K - - - - L V V H L Y H L C Q M    H.s. ENIP

466 Y N R E L S E - - - - E C R D Y I N E M Q A R - - - - - - Y K - - K N H F D A L    S.c. ENIP
493 F P S A L G I - - - - S F I S V V E G M R K R L A K S Y V Y P - - E I K F P E I    S.p. ENIP
461 - - E T M H A L M K F D I Q Y G V R C V R A L I R Q H W K G R Q D K Q K S S P V    C.e. ENIP
525 F P E S A S D A I K F V L R D A M H E M E E M I - - - - - - - E T K G R A A L P    H.s. ENIP

494 S N G D L V F F S I I G I L F S T S D Q Y H L V I T P A L I L M S Q F L - - E Q    S.c. ENIP
527 S - - D L F F N L T G S I F P T S D K K H I V V S P V M L T M A E S L - - S Q    S.p. ENIP
499 S F G L I S A I R L V S G L F P V A D S W H P V V V P A L F L A T E A L C S A K    C.e. ENIP
558 G L D V L I Y L K I T G L L F P T S D F W H P V V T P A L V C L S Q L L - - T K    H.s. ENIP

532 I K F N S L K R I A F G A V L V R I V S Q Y Q R I S K R Y I P E V V Y F F Q K I    S.c. ENIP
563 S P A D S L S D V C K L Y I A N L F L K F Q S Y S H R Y V P E V I T A V S Q A    S.p. ENIP
539 C A - - N L N A L A K Q I Q L A N A I V E Y V S E S K R Y V P E L V A F A R S A    C.e. ENIP
596 C P I L S L Q D V V K G L F V C C L F L E Y V A L S Q R F I P E L I N F L L G I    H.s. ENIP

572 L L T F I V E K E N Q E K P L - - - - - - - - - - - - - - - - - - - - - - - - -    S.c. ENIP
603 L Y L L Y P - - - - - - - - - - - - - - - - - - - - - - - - - - - - - - - - -    S.p. ENIP
577 L L L A V T E K S E K F A T - - N G F P I S K P H T E M L C F E E K L L F L T K    C.e. ENIP
636 L Y I A T P N K A S Q G S T L V H P F R A L G K N S E L L V - - - - - - - - - -    H.s. ENIP

587 D F E N I R L D S Y E L G L P L D V D - - - F T K K R S T I I P L H - - - - T L    S.c. ENIP
609 N F I S I V P G T F A L P D S L K E K Q N L F A I Q D I S L D E P Q - - - - R L    S.p. ENIP
615 N Y N W I S Q K E F D L S S F N R Y I D E L Y L K M T R K Y T G P A L Q P I S L    C.e. ENIP
666 - - - - V S A R E - D V A T W Q Q - - S S L S L R W A S R L R A P T - - - - - -    H.s. ENIP

620 S T M D T E A H P V D Q - C V S V L L N V M E S L D A T I S T V W K S L P A F N    S.c. ENIP
645 S L Y E L E E L P T G L L Q S S I L F I T L N L I E M A I D I Y F K E - Q A F I    S.p. ENIP
655 T T I F N N S P S D P S L K L H V L R A L L S L I Q H L R V I Y S N Q N E T Y S    C.e. ENIP
693 - - - - - - S T E A N H I R L S C L A V G L A L L K R C V L M Y G S L P S - - -    H.s. ENIP

659 E I I L P I Q Q L L S A Y T S K Y S D F E K - - P R N I L N K V - E K L T K F T    S.c. ENIP
684 E I F V P I M D M L Q L Y S L K K E L L S K R L S E K L L S T L - Q A V S D S I    S.p. ENIP
695 I V F K P F L R I L E - - S I Q A K N L P A - E V Q E E L E T L C A S M K A E I    C.e. ENIP
724 - - F H A I M G P L Q - - A L L T D H L A D C S H P Q E L Q E L C Q S T L T E M    H.s. ENIP

696 E - - - - - H I P L A L Q N H K P V S I P T H A P K Y E E N F N P D K K S Y D P    S.c. ENIP
723 E S A K A N R K P L A L Q S H R P L G I T S Q V P K F E E G Y S L D K S S H D I    S.p. ENIP
732 G A K C R L V H - L S L V K T E K S M L K M L E P R F E W D F D P E R P - H H G    C.e. ENIP
760 E S Q K Q L C R P L T C E K S K P V P L K L F T P R L V K V L E F G R K - Q G S    H.s. ENIP

731 D R T R S E I N K M K A Q L K K E R K F T M K E I R K D A K F E A R Q R I E E K    S.c. ENIP
763 D P E R A Q L N K L R A Q H R D A K K G A I R T L R K D A R F I A R E R R Q E Q    S.p. ENIP
770 P K D E - - K K K L T K N L R N E R R G A I K E L R K D T A F L A R K Q L S S V    C.e. ENIP
799 S K E E Q E R K R L I H K H K R E F K G A V R E I R K D N Q F L A R M Q L S E I    H.s. ENIP

771 N K E S S D Y H A K M A H I V N T I N T E E G A - E K N K Y E R E R K L R G G K    S.c. ENIP
803 R A K D Q A Y N E K M R K L E N R L Q - - - - - - - - - - H F D P A V              S.p. ENIP
808 K T K D R A R I A A T K R V M G G L M Q Q G E W N K E K R T A D V E K K K D K    C.e. ENIP
839 M E R D A E R K R K V K Q L F N S L A T Q E G E W K A L K R - - - - - - K K F K    H.s. ENIP

810 K                                                                                  S.c. ENIP
827                                                                                    S.p. ENIP
848 K                                                                                  C.e. ENIP
873 K                                                                                  H.s. ENIP
```

FIGURE 14B

SEQUENCE LISTING

```
<160> NUMBER OF SEQ ID NOS:  28

<210> SEQ ID NO 1
<211> LENGTH: 252
<212> TYPE: PRT
<213> ORGANISM: Saccharomyces cerevisiae

<400> SEQUENCE: 1
```

-continued

```
Met Val Glu Asp Ser Arg Val Arg Asp Ala Leu Lys Gly Gly Asp Gln
1               5                   10                  15

Lys Ala Leu Pro Ala Ser Leu Val Pro Gln Ala Pro Pro Val Leu Thr
            20                  25                  30

Ser Lys Asp Lys Ile Thr Lys Arg Met Ile Val Val Leu Ala Met Ala
        35                  40                  45

Ser Leu Glu Thr His Lys Ile Ser Ser Asn Gly Pro Gly Gly Asp Lys
    50                  55                  60

Tyr Val Leu Leu Asn Cys Asp His Gln Gly Leu Leu Lys Lys Met
65                  70                  75                  80

Gly Arg Asp Ile Ser Glu Ala Arg Pro Asp Ile Thr His Gln Cys Leu
                85                  90                  95

Leu Thr Leu Leu Asp Ser Pro Ile Asn Lys Ala Gly Lys Leu Gln Val
                100                 105                 110

Tyr Ile Gln Thr Ser Arg Gly Ile Leu Ile Glu Val Asn Pro Thr Val
            115                 120                 125

Arg Ile Pro Arg Thr Phe Lys Arg Phe Ser Gly Leu Met Val Gln Leu
    130                 135                 140

Leu His Lys Leu Ser Ile Arg Ser Val Asn Ser Glu Lys Leu Leu
145                 150                 155                 160

Lys Val Ile Lys Asn Pro Ile Thr Asp His Leu Pro Thr Lys Cys Arg
                165                 170                 175

Lys Val Thr Leu Ser Phe Asp Ala Pro Val Ile Arg Val Gln Asp Tyr
            180                 185                 190

Ile Glu Lys Leu Asp Asp Asp Glu Ser Ile Cys Val Phe Val Gly Ala
        195                 200                 205

Met Ala Arg Gly Lys Asp Asn Phe Ala Asp Glu Tyr Val Asp Glu Lys
    210                 215                 220

Val Gly Leu Ser Asn Tyr Pro Leu Ser Ala Ser Val Ala Cys Ser Lys
225                 230                 235                 240

Phe Cys His Gly Ala Glu Asp Ala Trp Asn Ile Leu
                245                 250
```

<210> SEQ ID NO 2
<211> LENGTH: 359
<212> TYPE: PRT
<213> ORGANISM: Schizosaccharomyces pombe

<400> SEQUENCE: 2

```
Met Pro Thr Tyr Ser Lys Arg Lys Ser Arg Gly Ser Leu Glu Val Ser
1               5                   10                  15

Glu Lys Thr Asn Gln Pro Lys Phe Ile Lys Arg Ser Gln Ser Ser Glu
            20                  25                  30

Thr Ile Thr Ser Gly Glu Thr Ala Ser Glu Leu Met Gln Asp Glu Lys
        35                  40                  45

Glu Gln Ser Asn Gly Ala Val Gly Ser Ile Glu Asp Glu Leu Gln
    50                  55                  60

Arg Leu Arg Glu Asn Gln Ala Ser Val Glu Ala Leu Ser Lys Lys Pro
65                  70                  75                  80

Glu Ser Ile Asp Arg Glu Leu Gly Val Glu Ala Leu Glu Ile Asp Asn
                85                  90                  95

Val Val Lys Ser Asp Glu Glu Lys Glu Asp Pro Asn Gly Ala Ser Ser
                100                 105                 110

Lys Thr Val Lys Ala Arg Pro Leu Pro Ala Gly Ser Val His Arg Val
            115                 120                 125
```

Thr Thr His Met Ala Pro Ile Pro Ala Arg Ser Ile Gly Ser His Asp
        130                 135                 140

Thr Thr Thr Gln Arg Leu Ile Val Val Leu Asp Gln Ala Cys Leu Glu
145                 150                 155                 160

Ile Tyr Lys Val Gly Lys Ala Lys Asp Ala Lys Tyr Gln Leu Leu Asn
                165                 170                 175

Cys Asp Asp His Gln Gly Ile Leu Lys Lys Leu Asn Arg Asn Ile Ala
            180                 185                 190

Gln Ala Arg Pro Asp Ile Thr His Gln Cys Leu Leu Thr Leu Leu Asp
        195                 200                 205

Ser Pro Leu Asn Lys Ala Gly Arg Leu Gln Val Tyr Ile His Thr Ala
    210                 215                 220

Lys Lys Val Leu Ile Glu Val Asn Pro Ser Val Arg Ile Pro Arg Thr
225                 230                 235                 240

Phe Lys Arg Phe Ser Gly Leu Met Val Gln Leu Leu His Lys Leu Ser
                245                 250                 255

Ile Arg Ser Val Asn Gly Asn Glu Lys Leu Leu Lys Val Ile Lys Asn
            260                 265                 270

Pro Val Thr Asp Tyr Leu Pro Pro Asn Cys Arg Lys Ala Thr Leu Ser
        275                 280                 285

Phe Asp Ala Pro Thr Val Pro Pro Arg Lys Tyr Leu Glu Thr Leu Gln
    290                 295                 300

Pro Asn Gln Ser Val Cys Ile Ala Ile Gly Ala Met Ala His Gly Pro
305                 310                 315                 320

Asp Asp Phe Ser Asp Gly Trp Val Asp Glu Lys Ile Ser Ile Ser Asp
                325                 330                 335

Tyr Pro Leu Ser Ala Ser Ile Ala Cys Ser Lys Phe Leu His Ser Met
            340                 345                 350

Glu Asp Phe Leu Gly Ile Val
        355

<210> SEQ ID NO 3
<211> LENGTH: 231
<212> TYPE: PRT
<213> ORGANISM: Caenorhabditis elegans

<400> SEQUENCE: 3

Met Ser His Glu Tyr Asp Thr Val Ala Pro Pro Asn Ala Lys Arg Met
1               5                   10                  15

Lys Thr Asp Asn Gln Leu Glu Asp Lys Lys Ile Leu Tyr Val Val Leu
            20                  25                  30

Glu Gly Cys Ser Leu Glu Thr Ala Lys Val Gly Gly Glu Tyr Ala Ile
        35                  40                  45

Leu Ser Ser Asp Lys His Ala Asn Phe Leu Arg Lys Gln Leu Lys Asp
    50                  55                  60

Pro Ala Asp Tyr Arg Pro Asp Ile Leu His Gln Cys Leu Leu Asn Leu
65                  70                  75                  80

Leu Asp Ser Pro Leu Asn Arg Ala Gly Lys Leu Arg Val Phe Phe Arg
                85                  90                  95

Thr Ser Lys Asn Val Leu Val Asp Val Ser Pro Gln Cys Arg Ile Pro
            100                 105                 110

Arg Thr Phe Asp Arg Phe Cys Gly Leu Met Val Gln Leu Leu His Lys
        115                 120                 125

Leu Ser Ile Arg Ala Ala Glu Thr Thr Gln Lys Leu Met Ser Val Val

```
                130             135             140
Lys Asn Pro Val Ser Asn His Leu Pro Val Gly Ser Arg Lys Met Leu
145                 150                 155                 160

Met Ser Phe Asn Val Pro Glu Leu Thr Met Ala Asn Lys Leu Val Ala
                165                 170                 175

Pro Glu Thr Asp Glu Pro Leu Val Leu Ile Ile Gly Gly Ile Ala Arg
            180                 185                 190

Gly Lys Ile Val Val Asp Tyr Asn Asp Ser Glu Thr Lys Ile Ser Asn
            195                 200                 205

Tyr Pro Leu Ser Ala Ala Leu Thr Cys Ala Lys Val Thr Ser Gly Leu
            210                 215                 220

Glu Glu Ile Trp Gly Ile Ile
225                 230

<210> SEQ ID NO 4
<211> LENGTH: 244
<212> TYPE: PRT
<213> ORGANISM: Mus musculus

<400> SEQUENCE: 4

Met Ser Ala Ala Ser Gly Gly Phe Gln Pro Arg Glu Arg Arg Phe Ser
1               5                   10                  15

Val Gln Glu Gln Asp Trp Glu Thr Thr Pro Pro Lys Lys Leu Arg Leu
            20                  25                  30

Gly Ala Gly Ser Lys Cys Gly Gly Arg Arg Leu Ile Val Val Leu Glu
        35                  40                  45

Gly Ala Ser Leu Glu Thr Val Lys Val Gly Lys Thr Tyr Glu Leu Leu
    50                  55                  60

Asn Cys Asp Arg His Lys Ser Met Leu Leu Lys Asn Gly Arg Asp Pro
65                  70                  75                  80

Gly Glu Val Arg Pro Asp Ile Thr His Gln Ser Leu Leu Met Leu Met
                85                  90                  95

Asp Ser Pro Leu Asn Arg Ala Gly Leu Leu Gln Val Tyr Ile His Thr
            100                 105                 110

Gln Lys Asn Val Leu Ile Glu Val Asn Pro Gln Thr Arg Ile Pro Arg
        115                 120                 125

Thr Phe Asp Arg Phe Cys Gly Leu Met Val Gln Leu Leu His Lys Leu
    130                 135                 140

Ser Val Arg Ala Ala Asp Gly Pro Gln Lys Leu Leu Lys Val Ile Lys
145                 150                 155                 160

Asn Pro Val Ser Asp His Phe Pro Val Gly Cys Met Lys Ile Gly Thr
                165                 170                 175

Ser Phe Ser Val Glu Asp Ile Ser Asp Ile Arg Glu Leu Val Pro Ser
            180                 185                 190

Ser Asp Pro Val Val Phe Val Val Gly Ala Phe Ala His Gly Lys Val
        195                 200                 205

Ser Val Glu Tyr Thr Glu Lys Met Val Ser Ile Ser Asn Tyr Pro Leu
    210                 215                 220

Ser Ala Ala Leu Thr Cys Ala Lys Val Thr Thr Ala Phe Glu Glu Val
225                 230                 235                 240

Trp Gly Val Ile

<210> SEQ ID NO 5
<211> LENGTH: 239
<212> TYPE: PRT
```

<213> ORGANISM: Homo sapiens

<400> SEQUENCE: 5

```
Asp Gly Phe Lys Pro Arg Glu Arg Ser Gly G ly Glu Gln Ala Gln Asp
1               5                   10                  15

Trp Asp Ala Leu Pro Pro Lys Arg Pro Arg L eu Gly Ala Gly Asn Lys
            20                  25                  30

Ile Gly Gly Arg Arg Leu Ile Val Val Leu G lu Gly Ala Ser Leu Glu
        35                  40                  45

Thr Val Lys Val Gly Lys Thr Tyr Glu Leu L eu Asn Cys Asp Lys His
    50                  55                  60

Lys Ser Ile Leu Leu Lys Asn Gly Arg Asp P ro Gly Glu Ala Arg Pro
65                  70                  75                  80

Asp Ile Thr His Gln Ser Leu Leu Met Leu M et Asp Ser Pro Leu Asn
                85                  90                  95

Arg Ala Gly Leu Leu Gln Val Tyr Ile His T hr Gln Lys Asn Val Leu
            100                 105                 110

Ile Glu Val Asn Pro Gln Thr Arg Ile Pro A rg Thr Phe Asp Arg Phe
        115                 120                 125

Cys Gly Leu Met Val Gln Leu Leu His Lys L eu Ser Val Arg Ala Ala
    130                 135                 140

Asp Gly Pro Gln Lys Leu Leu Lys Val Ile L ys Asn Pro Val Ser Asp
145                 150                 155                 160

His Phe Pro Val Gly Cys Met Lys Val Gly T hr Ser Phe Ser Ile Pro
                165                 170                 175

Val Val Ser Asp Val Arg Glu Leu Val Pro S er Ser Asp Pro Ile Val
            180                 185                 190

Phe Val Val Gly Ala Phe Ala His Gly Lys V al Ser Val Glu Tyr Thr
        195                 200                 205

Glu Lys Met Val Ser Ile Ser Asn Tyr Pro L eu Ser Ala Ala Leu Thr
    210                 215                 220

Cys Ala Lys Leu Thr Thr Ala Phe Glu Glu V al Trp Gly Val Ile
225                 230                 235
```

<210> SEQ ID NO 6
<211> LENGTH: 720
<212> TYPE: DNA
<213> ORGANISM: Homo sapiens

<400> SEQUENCE: 6

```
gatggattca agcctcgtga acgaagcggt ggggagcagg cacaggactg g gatgctctg    60
ccacccaagc ggccccgact aggggcagga aacaagatcg gaggccgtag g cttattgtg   120
gtgctggaag gggccagtct ggagacagtc aaggtaggga agacatatga g ctactcaac   180
tgtgacaagc acaagtctat attgttgaag aatggacggg accctgggga a gcgcggcca   240
gatatcaccc accagagttt gctgatgctg atggatagtc ccctgaaccg a gctggcttg   300
ctacaggttt atatccatac acagaagaat gttctgattg aagtgaatcc c agacccga   360
attcccagaa cctttgaccg cttttgtggc ctcatggttc aactttttaca c aagctcagt   420
gttcgagcag ctgatggccc ccagaagctt ttgaaggtaa ttaagaatcc a gtatcagat   480
cactttccag ttggatgtat gaaagttggc acttcttttt ccatcccggt t gtcagtgat   540
gtgcgtgagc tggtgcccag cagtgatcct attgtttttg tggtaggggc c tttgcccat   600
ggcaaggtca gtgtggagta tacagagaag atggtgtcca tcagtaacta c cccctttct   660
```

-continued gctgccctca cctgtgcaaa acttaccaca gcctttgagg aagtatgggg g gtcatttga    720

<210> SEQ ID NO 7
<211> LENGTH: 239
<212> TYPE: PRT
<213> ORGANISM: Homo sapiens

<400> SEQUENCE: 7

Asp Gly Phe Lys Pro Arg Glu Arg Ser Gly G ly Glu Gln Ala Gln Asp
1               5                   10                  15

Trp Asp Ala Leu Pro Pro Lys Arg Pro Arg L eu Gly Ala Gly Asn Lys
            20                  25                  30

Ile Gly Gly Arg Arg Leu Ile Val Val Leu G lu Gly Ala Ser Leu Glu
        35                  40                  45

Thr Val Lys Val Gly Lys Thr Tyr Glu Leu L eu Asn Cys Asp Lys His
    50                  55                  60

Lys Ser Ile Leu Leu Lys Asn Gly Arg Asp P ro Gly Glu Ala Arg Pro
65                  70                  75                  80

Asp Ile Thr His Gln Ser Leu Leu Met Leu M et Asp Ser Pro Leu Asn
                85                  90                  95

Arg Ala Gly Leu Leu Gln Val Tyr Ile His T hr Gln Lys Asn Val Leu
            100                 105                 110

Ile Glu Val Asn Pro Gln Thr Arg Ile Pro A rg Thr Phe Asp Arg Phe
        115                 120                 125

Cys Gly Leu Met Val Gln Leu Leu His Lys L eu Ser Val Arg Ala Ala
    130                 135                 140

Asp Gly Pro Gln Lys Leu Leu Lys Val Ile L ys Asn Pro Val Ser Asp
145                 150                 155                 160

His Phe Pro Val Gly Cys Met Lys Val Gly T hr Ser Phe Ser Ile Pro
                165                 170                 175

Val Val Ser Asp Val Arg Glu Leu Val Pro S er Ser Asp Pro Ile Val
            180                 185                 190

Phe Val Val Gly Ala Phe Ala His Gly Lys V al Ser Val Glu Tyr Thr
        195                 200                 205

Glu Lys Met Val Ser Ile Ser Asn Tyr Pro L eu Ser Ala Ala Leu Thr
    210                 215                 220

Cys Ala Lys Leu Thr Thr Ala Phe Glu Glu V al Trp Gly Val Ile
225                 230                 235

<210> SEQ ID NO 8
<211> LENGTH: 759
<212> TYPE: DNA
<213> ORGANISM: Saccharomyces cerevisiae

<400> SEQUENCE: 8
atggtcgaag attccagagt tagagacgcc ctcaaggtg gtgatcagaa g cattaccg      60 gcctctttgg ttcctcaagc acctcctgtc ttgacatcaa aggataagat t actaagcgg   120 atgattgtgg tattagcgat ggcatccctc gagacacaca agatatcgtc c aacgggcct   180 ggtggtgaca aatatgtcct tttgaactgt gacgaccatc aaggtttatt a aaaaaaatg   240 ggtagagaca ttagtgaagc aagacctgat attacccacc aatgtctttt g acgttgcta   300 gattctccaa tcaacaaagc cggaaagctg caggtctata ttcaaacaag t cgaggaatt   360 ctgatcgagg ttaaccccac tgttcgtata ccaagaactt tcaaaagatt t caggttta   420 atggttcagt tactacataa gctttctatc agatcggtaa attctgaaga a aagttactt   480

-continued

```
aaagtcatta agaacccaat taccgatcac ctacctacta agtgccgtaa g gtgacatta      540 tcctttgacg caccagttat ccgcgttcaa gattacatcg aaaaactaga c gatgatgaa      600 agtatatgtg tctttgttgg tgccatggca agaggtaaag ataactttgc g gatgaatac      660 gtcgacgaaa aagtcggctt gtccaattac ccattgtctg cctcagttgc a tgttctaaa      720 ttttgccatg gcgctgaaga tgcttggaat attttatag                              759
```

<210> SEQ ID NO 9
<211> LENGTH: 251
<212> TYPE: PRT
<213> ORGANISM: Saccharomyces cerevisiae

<400> SEQUENCE: 9

```
Met Val Glu Asp Ser Arg Val Arg Asp Ala Leu Lys Gly Gly Asp Gln
1               5                   10                  15

Lys Ala Leu Pro Ala Ser Leu Val Pro Gln Ala Pro Pro Val Leu Thr
            20                  25                  30

Ser Lys Asp Lys Ile Thr Lys Arg Met Ile Val Val Leu Ala Met Ala
        35                  40                  45

Ser Leu Glu Thr His Lys Ile Ser Ser Asn Gly Pro Gly Gly Asp Lys
    50                  55                  60

Tyr Val Leu Leu Asn Cys Asp Asp His Gln Gly Leu Leu Lys Lys Met
65                  70                  75                  80

Gly Arg Asp Ile Ser Glu Ala Arg Pro Asp Ile Thr His Gln Cys Leu
                85                  90                  95

Leu Thr Leu Leu Asp Ser Pro Ile Asn Lys Ala Gly Lys Leu Gln Val
            100                 105                 110

Tyr Gln Thr Ser Arg Gly Ile Leu Ile Glu Val Asn Pro Thr Val Arg
        115                 120                 125

Ile Pro Arg Thr Phe Lys Arg Phe Ser Gly Leu Met Val Gln Leu Leu
    130                 135                 140

His Lys Leu Ser Ile Arg Ser Val Asn Ser Glu Glu Lys Leu Leu Lys
145                 150                 155                 160

Val Ile Lys Asn Pro Ile Thr Asp His Leu Pro Thr Lys Cys Arg Lys
                165                 170                 175

Val Thr Leu Ser Phe Asp Ala Pro Val Ile Arg Val Gln Asp Tyr Ile
            180                 185                 190

Glu Lys Leu Asp Asp Asp Glu Ser Ile Cys Val Phe Val Gly Ala Met
        195                 200                 205

Ala Arg Gly Lys Asp Asn Phe Ala Asp Glu Tyr Val Asp Glu Lys Val
    210                 215                 220

Gly Leu Ser Asn Tyr Pro Leu Ser Ala Ser Val Ala Cys Ser Lys Phe
225                 230                 235                 240

Cys His Gly Ala Glu Asp Ala Trp Asn Ile Leu
                245                 250
```

<210> SEQ ID NO 10
<211> LENGTH: 735
<212> TYPE: DNA
<213> ORGANISM: Mus musculus

<400> SEQUENCE: 10

```
atgtctgcgg ccagtggtgg cttccaacct cgtgagcggc gattttcagt g caggagcag      60 gactgggaga ctacgccgcc taagaagctc cggcttgggg caggaagcaa g tgcggaggc     120 cggaggctca ttgtggtgct ggaagggggcc agtctggaga cagtcaaggt a gggaaaact    180
```

```
tacgagctac tcaactgtga caggcacaag tccatgttgt tgaagaatgg a cgggaccca    240 ggggaagtca gaccagacat cacccaccag agcctgctga tgcttatgga c agcccctg    300 aaccgagctg gcttgctaca ggtttacatc cacacacaga agaacgtgct g attgaagtg    360 aaccccaga ctcgaattcc tagaacctt gaccgatttt gtggcctcat g gttcagctt    420 ttacacaaac tgagcgtccg agcagccgac ggccctcaga agctattgaa g gtaattaag    480 aatccagtgt ccgaccactt cccagttggc tgtatgaaaa ttggcacttc c ttttctgtt    540 gaagacatca gtgacattcg agagttggtg cccagtagtg acccagttgt g tttgtggtg    600 ggggcctttg cccatggcaa ggtcagtgtg gagtacacag aaaagatggt g tccatcagc    660 aactatccac tctctgctgc gcttacctgt gctaaagtca ccacagcttt t gaagaagta    720 tggggtgtca tttga                                                      735
```

```
<210> SEQ ID NO 11
<211> LENGTH: 244
<212> TYPE: PRT
<213> ORGANISM: Mus musculus

<400> SEQUENCE: 11

Met Ser Ala Ala Ser Gly Gly Phe Gln Pro A rg Glu Arg Arg Phe Ser
1               5                  10                  15

Val Gln Glu Gln Asp Trp Glu Thr Thr Pro P ro Lys Lys Leu Arg Leu
            20                  25                  30

Gly Ala Gly Ser Lys Cys Gly Gly Arg Arg L eu Ile Val Val Leu Glu
        35                  40                  45

Gly Ala Ser Leu Glu Thr Val Lys Val Gly L ys Thr Tyr Glu Leu Leu
    50                  55                  60

Asn Cys Asp Arg His Lys Ser Met Leu Leu L ys Asn Gly Arg Asp Pro
65                  70                  75                  80

Gly Glu Val Arg Pro Asp Ile Thr His Gln S er Leu Leu Met Leu Met
                85                  90                  95

Asp Ser Pro Leu Asn Arg Ala Gly Leu Leu G ln Val Tyr Ile His Thr
            100                 105                 110

Gln Lys Asn Val Leu Ile Glu Val Asn Pro G ln Thr Arg Ile Pro Arg
        115                 120                 125

Thr Phe Asp Arg Phe Cys Gly Leu Met Val G ln Leu Leu His Lys Leu
    130                 135                 140

Ser Val Arg Ala Ala Asp Gly Pro Gln Lys L eu Leu Lys Val Ile Lys
145                 150                 155                 160

Asn Pro Val Ser Asp His Phe Pro Val Gly C ys Met Lys Ile Gly Thr
                165                 170                 175

Ser Phe Ser Val Glu Asp Ile Ser Asp Ile A rg Glu Leu Val Pro Ser
            180                 185                 190

Ser Asp Pro Val Val Phe Val Val Gly Ala P he Ala His Gly Lys Val
        195                 200                 205

Ser Val Glu Tyr Thr Glu Lys Met Val Ser I le Ser Asn Tyr Pro Leu
    210                 215                 220

Ser Ala Ala Leu Thr Cys Ala Lys Val Thr T hr Ala Phe Glu Glu Val
225                 230                 235                 240

Trp Gly Val Ile

<210> SEQ ID NO 12
<211> LENGTH: 27
```

<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic

<400> SEQUENCE: 12
cgaattccca gaacctttga ccgcttt                                              27

<210> SEQ ID NO 13
<211> LENGTH: 24
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic

<400> SEQUENCE: 13
cgaattccca gaacctttga ccgc                                                 24

<210> SEQ ID NO 14
<211> LENGTH: 18
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic

<400> SEQUENCE: 14
attcccagaa cctttgac                                                        18

<210> SEQ ID NO 15
<211> LENGTH: 15
<212> TYPE: DNA
<213> ORGANISM: Artificial/Unknown
<220> FEATURE:
<221> NAME/KEY: misc_feature
<222> LOCATION: ()..()
<223> OTHER INFORMATION: Synthetic

<400> SEQUENCE: 15
attcccagaa ccttt                                                           15

<210> SEQ ID NO 16
<211> LENGTH: 805
<212> TYPE: DNA
<213> ORGANISM: Drosophila Emg1

<400> SEQUENCE: 16
aataatttcg gaattgtttt taaccatata caactacttt tacgatatgg g cggtcaggg         60 caaggcgatc aataggaagc gtaagtttgt cggtcgcaag gcggacgatc c ggagttcga        120 tctggacaag aagcaattca aggtgctcca tctgaatgcc accgaaaagc g gctgatcat        180 cgttttggaa ggagcccaac tggagacggt gaaggtgcac aacactttca a gctgctgaa       240 ctgcgacgat cacgcgggaa ttatgcgcaa aaaccaaaga gatcccggct c ctgccgttc        300 ggacatcacc caccaatgcc tgttgatgct ctttgattcg ccactgaacc g gccggtct        360 gcttcaggtc tttgtgcgca ccgagcataa tgtgcttatc gaaatcaatc c ccagacgcg       420 catcccgagg acatttaaac gctttgctgg cctaatggtg caattgctgc a caagttcca      480 aattcgcgcc aatgactcct cacgtcgtct gatgagtgtc attaagaatc c gattacgga      540

```
tcatgtgccg gtcggttgca agaagtacgc catgagcttc tctggcaaac t attgcccaa     600 ttgccgggat ctggtgccac atggtgacga gacgtcggcc agctatgatg a gccggtggt     660 catcgttatt ggagccttcg cacatggcgt tctcaaaacg gactacacgg a ggagctgtt     720 ctccattagc aactatccac tttcggcggc catcgcgtgc tccaaaatct g ttccgcctt     780 cgaggaggtt tggggcgtgg tataa                                             805
```

<210> SEQ ID NO 17
<211> LENGTH: 252
<212> TYPE: PRT
<213> ORGANISM: Drosophila Emg1

<400> SEQUENCE: 17

```
Met Gly Gly Gln Gly Lys Ala Ile Asn Arg L ys Arg Lys Phe Val Gly
1               5                   10                  15

Arg Lys Ala Asp Asp Pro Glu Phe Asp Leu A sp Lys Lys Gln Phe Lys
            20                  25                  30

Val Leu His Leu Asn Ala Thr Glu Lys Arg L eu Ile Ile Val Leu Glu
        35                  40                  45

Gly Ala Gln Leu Glu Thr Val Lys Val His A sn Thr Phe Lys Leu Leu
    50                  55                  60

Asn Cys Asp Asp His Ala Gly Ile Met Arg L ys Asn Gln Arg Asp Pro
65                  70                  75                  80

Gly Ser Cys Arg Ser Asp Ile Thr His Gln C ys Leu Leu Met Leu Phe
                85                  90                  95

Asp Ser Pro Leu Asn Arg Ala Gly Leu Leu G ln Val Phe Val Arg Thr
            100                 105                 110

Glu His Asn Val Leu Ile Glu Ile Asn Pro G ln Thr Arg Ile Pro Arg
        115                 120                 125

Thr Phe Lys Arg Phe Ala Gly Leu Met Val G ln Leu Leu His Lys Phe
    130                 135                 140

Gln Ile Arg Ala Asn Asp Ser Ser Arg Arg L eu Met Ser Val Ile Lys
145                 150                 155                 160

Asn Pro Ile Thr Asp His Val Pro Val Gly C ys Lys Lys Tyr Ala Met
                165                 170                 175

Ser Phe Ser Gly Lys Leu Leu Pro Asn Cys A rg Asp Leu Val Pro His
            180                 185                 190

Gly Asp Glu Thr Ser Ala Ser Tyr Asp Glu P ro Val Val Ile Val Ile
        195                 200                 205

Gly Ala Phe Ala His Gly Val Leu Lys Thr A sp Tyr Thr Glu Glu Leu
    210                 215                 220

Phe Ser Ile Ser Asn Tyr Pro Leu Ser Ala A la Ile Ala Cys Ser Lys
225                 230                 235                 240

Ile Cys Ser Ala Phe Glu Glu Val Trp Gly V al Val
                245                 250
```

<210> SEQ ID NO 18
<211> LENGTH: 26
<212> TYPE: PRT
<213> ORGANISM: Saccharomyces cerevisiae

<400> SEQUENCE: 18

```
Thr His Gln Cys Leu Leu Thr Leu Leu Asp S er Pro Ile Asn Lys Ala
1               5                   10                  15

Gly Lys Leu Gln Val Tyr Ile Gln Thr Ser
            20                  25
```

<210> SEQ ID NO 19
<211> LENGTH: 26
<212> TYPE: PRT
<213> ORGANISM: Schizosaccharomyces pombe

<400> SEQUENCE: 19

Thr His Gln Cys Leu Leu Thr Leu Leu Asp S er Pro Leu Asn Lys Ala
1               5                   10                  15

Gly Arg Leu Gln Val Tyr Ile His Thr Ala
            20                  25

<210> SEQ ID NO 20
<211> LENGTH: 26
<212> TYPE: PRT
<213> ORGANISM: Caenorhabditis elegans

<400> SEQUENCE: 20

Leu His Gln Cys Leu Leu Asn Leu Leu Asp S er Pro Leu Asn Arg Ala
1               5                   10                  15

Gly Lys Leu Arg Val Phe Phe Arg Thr Ser
            20                  25

<210> SEQ ID NO 21
<211> LENGTH: 26
<212> TYPE: PRT
<213> ORGANISM: Mus musculus

<400> SEQUENCE: 21

Thr His Gln Ser Leu Leu Met Leu Met Asp S er Pro Leu Asn Arg Ala
1               5                   10                  15

Gly Leu Leu Gln Val Tyr Ile His Thr Gln
            20                  25

<210> SEQ ID NO 22
<211> LENGTH: 26
<212> TYPE: PRT
<213> ORGANISM: Homo sapiens

<400> SEQUENCE: 22

Thr His Gln Ser Leu Leu Met Leu Met Asp S er Pro Leu Asn Arg Ala
1               5                   10                  15

Gly Leu Leu Gln Val Tyr Ile His Thr Gln
            20                  25

<210> SEQ ID NO 23
<211> LENGTH: 2623
<212> TYPE: DNA
<213> ORGANISM: Homo sapiens

<400> SEQUENCE: 23
cctgtctctc ttcgggtctc gggcccttgg gcgcagcggg gcgcgcgcca t ggcgaaggc     60 gaagaaggtc gggcgcgaa ggaaggcctc cggggcgccg gcgggagcgc g aggggcccc    120 ggcgaaggcc aactccaatc cgttcgaggt gaaagttaac aggcagaagt t ccagatcct   180 gggccggaag acgcgccacg acgtgggact gcccggggtg tctcgcgcac g ggccctcag   240 gaagcgtaca cagactttac taaagagta caaagaaagg gataaatcca a tgtattcag    300 agataaacgc ttcggagaat acaacagcaa catgagcccc gaggagaaga t gatgaagag   360 gtttgctctg gaacagcagc gacatcatga gaaaaaaagc atctacaatc t aaatgaaga   420

```
tgaagaattg actcattatg gccagtcttt ggcagacatc gagaagcata a tgacattgt    480 ggacagtgac agcgatgctg aggatcgagg aacgttgtct gctgagctga c tgctgccca    540 ctttggagga ggcggtgggc tccttcacaa gaagactcaa caggaaggcg a ggagcggga    600 gaaaccgaag tcccggaaag agctgattga agagctcatt gccaagtcaa a caagagaa    660 gagggagaga caagctcaac gagaagatgc cctcgagctc acggagaagc t agaccaaga   720 ctggaaagaa attcagactc tcctgtccca caaaactccc aagtcagaga a cagagacaa   780 aaaggaaaaa cccaagcccg atgcatatga catgatggtt cgcgagcttg g ctttgaaat   840 gaaggcgcag ccctctaaca ggatgaagac ggaggcagaa ttggcaaagg a gagcagga    900 gcacctcagg aagctggagg ctgagagact tcgaagaatg cttggaaagg a tgaggatga   960 aaatgttaag aaaccaaaac atatgtcagc agatgatctg aatgatggct t cgtgctaga  1020 taaagatgac aggcgtttgc tttcctacaa agatggaaag atgaatgtcg a ggaagatgt  1080 ccaggaagag caaagcaagg aagccagtga ccctgagagc aacgaggaag a aggtgacag  1140 ttcaggcggg gaggacacag aggagagcga cagcccagat agccacttgg a cctggaatc  1200 caacgtggag agtgaggaag aaaacgagaa gccagcaaaa gagcagaggc a gactcctgg  1260 gaaagggttg ataagcggca aggaaagagc tggaaaagct accagagacg a gctgcccta  1320 cacgttcgca gcccctgaat cctatgagga actgagatct ctgttgttag g aagatcgat  1380 ggaagagcag cttttggtgg tggagagaat tcagaagtgc aaccacccga g tctcgcaga  1440 aggaaacaaa gcaaaattag aaaaactgtt tggctttctt ttggaatacg t tggcgattt  1500 ggctacagat gacccaccag acctcacagt cattgataag ttggttgtgc a cttatatca  1560 tctttgccag atgtttcctg aatctgcaag tgacgctatc aaatttgttc t ccgagatgc  1620 gatgcatgag atggaagaaa tgattgagac caaaggccgg gcggcattgc c agggttgga  1680 tgtgctcatt tatttgaaaa tcactgggct gctatttcca acttccgact t ctggcaccc  1740 agtggtgacc cctgccctcg tgtgcctcag tcagctgctc accaagtgcc c catcctgtc  1800 cctccaggac gtggtgaagg gcctgttcgt gtgctgcctg ttcctggagt a tgtggcttt  1860 gtcccagagg tttatacctg agcttattaa ttttcttctt gggattcttt a catagcaac  1920 tccaaacaaa gcaagccaag gttccactct ggtgcaccct tcagagcgct t gggaagaa   1980 ctcggaactg ctcgtggtgt ctgctagaga ggatgtggcc acgtggcagc a gagcagcct  2040 ctccctccgc tgggcgagta gactgagggc cccaacttcg acagaggcca a tcacatccg  2100 actgtcctgc ctggctgtgg gcctggccct gctgaagcgc tgcgtgctca t gtacgggtc  2160 cctgccatcc ttccacgcca tcatgggcc tctccaagcc ctcctcacgg a tcacctggc  2220 ggactgcagc cacccgcagg agctccagga gctgtgtcag agcacactga c cgaaatgga  2280 aagccagaag cagctctgcc ggccgctgac ctgtgagaag agcaagcctg t cccactgaa  2340 gcttttcaca ccccggctgg tcaaagtcct cgagtttgga agaaaacaag g cagtagtaa  2400 ggaggaacag gaaaggaaga ggctgatcca caaacacaag cgtgaattta a aggggccgt  2460 tcgagaaatc cgcaaggaca atcagttcct ggcgaggatg caactctcag a aatcatgga  2520 acgggatgcg gaaagaaagc ggaaagtaaa gcagctttt aacagcctgg c tacacagga  2580 aggcgaatgg aaggctctga gaggaaaaa gttcaaaaaa taa                      2623
```

<210> SEQ ID NO 24
<211> LENGTH: 2433
<212> TYPE: DNA
<213> ORGANISM: Saccharomyces cerevisiae

<400> SEQUENCE: 24

```
atggccggtt cacaacttaa gaatttaaag gccgccttga aggcccgtgg a ctcacaggt      60
caaacaaacg tcaaaagtaa gaataaaaag aattccaaaa gacaagcgaa g gagtatgat     120
cgtgaagaaa aaaaaaaggc cattgctgaa atcagagaag agtttaatcc g tttgaaata    180
aaggctgcaa ggaataagag gagagatggt ctgccttcta aaactgctga t cgtattgct   240
gtgggtaagc ctggtatctc taaacagatc ggtgaagaac aaagaaagcg t gcatttgaa    300
gcaagaaaaa tgatgaagaa taacgtggt ggtgtgatcg ataagagatt t ggtgaaaga    360
gacaagttgt tgacggaaga agaaaaaatg ttggaacgtt tcaccagaga a agacaaagc    420
caatcaaaga gaaacgcaaa tttattcaat cttgaagacg atgaagacga c ggtgacatg   480
tttggagacg gtcttacaca tttaggtcaa tcgctgtccc tagaagatga g cttgccaat    540
gatgaagagg atttttagc ttccaaacga ttcaatgaag atgatgctga g ctacagcaa     600
cctcaaagaa aaaaaaccaa agctgaagtc atgaagaggt cattgccaa a tcaaaattt    660
tacaaacaag aaagacaaaa ggctcaaggt ataatggaag atcaaataga t aatctggat   720
gataatttcg aggatgttat gtctgaattg atgatgacgc aacccaagaa g aatccaatg    780
gaacctaaga ccgatctaga taaggagtat gatatcaaag tgaaagaact a caattggac    840
aaaagagctg caccctctga tagaactaaa actgaagagg agaaaacgc t gaagctgaa     900
gaaaaaaaac gggagttgga acaacagcgt cttgatcgta tgaacggtat g attgaatta    960
gaagaaggcg aagaagagg agtagaggat ttggatgatg gattctggga a aatgaagaa   1020
gactatgaag acgataatga cggtattgct gattctgatg atgatatcaa a tttgaagat   1080
caaggcagag atgaagggtt ttctcaaatt ttaagaaaaa agaacatttc c atttcatgc   1140
cctagaactc atgatgcgtt attagatcaa gtaaaaaaat tagacttaga t gatcatcct  1200
aagattgtta agaatattat caaagcttac caaccaaaat tggctgaagg t aataaggaa  1260
aagttaggaa aattcaccgc tgttttactg agacacatca ttttctaag c aatcaaaac   1320
taccttaaaa acgttcaaag ttttaaacgt acacaaaatg cattgatctc a attctaaaa  1380
tccctttcag agaaatataa tagagagctt tccgaggagt gtagagatta t atcaatgaa   1440
atgcaagcac gctataaaaa gaaccatttt gatgctctat caaatggtga t ctggtattt  1500
tttccatta ttggtattct tttctccacc tcggaccagt accatttagt a ataactcca     1560
gcattgattt taatgagcca gttcctggaa caaatcaagt ttaattcttt a agaggata     1620
gcttttggcg ctgtcttggt aaggattgtt tcacaatatc aacgcatttc c aaacggtac   1680
ataccggagg tggtttactt cttttcaaaaa atattactca ctttatagt t gagaaagaa  1740
aatcaagaaa aaccattaga ttttgaaaat attagactag actcttacga g ttgggctt     1800
ccattggacg ttgactttac aaaaaagaga tcaactatta ttccattaca t accttgtca    1860
acaatggata ccgaggcaca tccggttgat caatgtgtct ccgtttact a aatgttatg   1920
gaatctttag atgcaactat ctctactgtg tggaagagct tacctgcttt c aatgaaatt    1980
attttaccga ttcagcagtt attaagtgca tacacctcaa agtattctga t tttgaaaag   2040
ccaagaaata ttttgaacaa agttgaaaaa ttaacgaaat tcacagaaca t attccgttg    2100
gctttacaga accacaaacc cgtatccata cctacgcatg ctcctaaata c gaagaaaac   2160
ttcaatcctg ataaaaaatc gtacgatcct gatagaacaa gaagtgagat a aataagatg   2220
aaggcccaac taaagaagga acgtaaattc actatgaaag aaatccgtaa a gacgccaaa   2280
```

```
tttgaagcta gacaaagaat tgaagaaaag aacaaggaga gcagcgacta c catgcaaag    2340 atggctcata ttgttaacac tattaatacc gaagaaggtg cggaaaaaaa c aagtatgaa    2400 agagaaagaa aactacgtgg cggaaagaaa taa                                  2433
```

<210> SEQ ID NO 25
<211> LENGTH: 810
<212> TYPE: PRT
<213> ORGANISM: Saccharomyces cerevisiae

<400> SEQUENCE: 25

```
Met Ala Gly Ser Gln Leu Lys Asn Leu Lys Ala Ala Leu Lys Ala Arg
1               5                   10                  15

Gly Leu Thr Gly Gln Thr Asn Val Lys Ser Lys Asn Lys Lys Asn Ser
            20                  25                  30

Lys Arg Gln Ala Lys Glu Tyr Asp Arg Glu Glu Lys Lys Lys Ala Ile
        35                  40                  45

Ala Glu Ile Arg Glu Glu Phe Asn Pro Phe Glu Ile Lys Ala Ala Arg
    50                  55                  60

Asn Lys Arg Arg Asp Gly Leu Pro Ser Lys Thr Ala Asp Arg Ile Ala
65                  70                  75                  80

Val Gly Lys Pro Gly Ile Ser Lys Gln Ile Gly Glu Glu Gln Arg Lys
                85                  90                  95

Arg Ala Phe Glu Ala Arg Lys Met Met Lys Asn Lys Arg Gly Gly Val
            100                 105                 110

Ile Asp Lys Arg Phe Gly Glu Arg Asp Lys Leu Leu Thr Glu Glu Glu
        115                 120                 125

Lys Met Leu Glu Arg Phe Thr Arg Glu Arg Gln Ser Gln Ser Lys Arg
    130                 135                 140

Asn Ala Asn Leu Phe Asn Leu Glu Asp Asp Glu Asp Asp Gly Asp Met
145                 150                 155                 160

Phe Gly Asp Gly Leu Thr His Leu Gly Gln Ser Leu Ser Leu Glu Asp
                165                 170                 175

Glu Leu Ala Asn Asp Glu Glu Asp Phe Leu Ala Ser Lys Arg Phe Asn
            180                 185                 190

Glu Asp Asp Ala Glu Leu Gln Gln Pro Gln Arg Lys Lys Thr Lys Ala
        195                 200                 205

Glu Val Met Lys Glu Val Ile Ala Lys Ser Lys Phe Tyr Lys Gln Glu
    210                 215                 220

Arg Gln Lys Ala Gln Gly Ile Met Glu Asp Gln Ile Asp Asn Leu Asp
225                 230                 235                 240

Asp Asn Phe Glu Asp Val Met Ser Glu Leu Met Met Thr Gln Pro Lys
                245                 250                 255

Lys Asn Pro Met Glu Pro Lys Thr Asp Leu Asp Lys Glu Tyr Asp Ile
            260                 265                 270

Lys Val Lys Glu Leu Gln Leu Asp Lys Arg Ala Ala Pro Ser Asp Arg
        275                 280                 285

Thr Lys Thr Glu Glu Glu Lys Asn Ala Glu Ala Glu Lys Lys Arg
    290                 295                 300

Glu Leu Glu Gln Gln Arg Leu Asp Arg Met Asn Gly Met Ile Glu Leu
305                 310                 315                 320

Glu Glu Gly Glu Glu Arg Gly Val Glu Asp Leu Asp Asp Gly Phe Trp
                325                 330                 335

Glu Asn Glu Glu Asp Tyr Glu Asp Asp Asn Asp Gly Ile Ala Asp Ser
            340                 345                 350
```

```
Asp Asp Asp Ile Lys Phe Glu Asp Gln Gly Arg Asp Glu Gly Phe Ser
        355                 360                 365
Gln Ile Leu Lys Lys Lys Asn Ile Ser Ile Ser Cys Pro Arg Thr His
        370                 375                 380
Asp Ala Leu Leu Asp Gln Val Lys Lys Leu Asp Leu Asp Asp His Pro
385                 390                 395                 400
Lys Ile Val Lys Asn Ile Ile Lys Ala Tyr Gln Pro Lys Leu Ala Glu
                405                 410                 415
Gly Asn Lys Glu Lys Leu Gly Lys Phe Thr Ala Val Leu Leu Arg His
        420                 425                 430
Ile Ile Phe Leu Ser Asn Gln Asn Tyr Leu Lys Asn Val Gln Ser Phe
        435                 440                 445
Lys Arg Thr Gln Asn Ala Leu Ile Ser Ile Leu Lys Ser Leu Ser Glu
        450                 455                 460
Lys Tyr Asn Arg Glu Leu Ser Glu Glu Cys Arg Asp Tyr Ile Asn Glu
465                 470                 475                 480
Met Gln Ala Arg Tyr Lys Lys Asn His Phe Asp Ala Leu Ser Asn Gly
                485                 490                 495
Asp Leu Val Phe Phe Ser Ile Ile Gly Ile Leu Phe Ser Thr Ser Asp
                500                 505                 510
Gln Tyr His Leu Val Ile Thr Pro Ala Leu Ile Leu Met Ser Gln Phe
        515                 520                 525
Leu Glu Gln Ile Lys Phe Asn Ser Leu Lys Arg Ile Ala Phe Gly Ala
        530                 535                 540
Val Leu Val Arg Ile Val Ser Gln Tyr Gln Arg Ile Ser Lys Arg Tyr
545                 550                 555                 560
Ile Pro Glu Val Val Tyr Phe Phe Gln Lys Ile Leu Leu Thr Phe Ile
                565                 570                 575
Val Glu Lys Glu Asn Gln Glu Lys Pro Leu Asp Phe Glu Asn Ile Arg
        580                 585                 590
Leu Asp Ser Tyr Glu Leu Gly Leu Pro Leu Asp Val Asp Phe Thr Lys
        595                 600                 605
Lys Arg Ser Thr Ile Ile Pro Leu His Thr Leu Ser Thr Met Asp Thr
        610                 615                 620
Glu Ala His Pro Val Asp Gln Cys Val Ser Val Leu Leu Asn Val Met
625                 630                 635                 640
Glu Ser Leu Asp Ala Thr Ile Ser Thr Val Trp Lys Ser Leu Pro Ala
                645                 650                 655
Phe Asn Glu Ile Ile Leu Pro Ile Gln Gln Leu Leu Ser Ala Tyr Thr
                660                 665                 670
Ser Lys Tyr Ser Asp Phe Glu Lys Pro Arg Asn Ile Leu Asn Lys Val
        675                 680                 685
Glu Lys Leu Thr Lys Phe Thr Glu His Ile Pro Leu Ala Leu Gln Asn
        690                 695                 700
His Lys Pro Val Ser Ile Pro Thr His Ala Pro Lys Tyr Glu Glu Asn
705                 710                 715                 720
Phe Asn Pro Asp Lys Lys Ser Tyr Asp Pro Asp Arg Thr Arg Ser Glu
                725                 730                 735
Ile Asn Lys Met Lys Ala Gln Leu Lys Lys Glu Arg Lys Phe Thr Met
                740                 745                 750
Lys Glu Ile Arg Lys Asp Ala Lys Phe Glu Ala Arg Gln Arg Ile Glu
        755                 760                 765
```

```
Glu Lys Asn Lys Glu Ser Ser Asp Tyr His Ala Lys Met Ala His Ile
            770             775             780

Val Asn Thr Ile Asn Thr Glu Glu Gly Ala Glu Lys Asn Lys Tyr Glu
785             790             795             800

Arg Glu Arg Lys Leu Arg Gly Gly Lys Lys
                805             810

<210> SEQ ID NO 26
<211> LENGTH: 825
<212> TYPE: PRT
<213> ORGANISM: Schizosaccharomyces pombe

<400> SEQUENCE: 26

Met Gly Lys Asn Gly Ser Gln Leu Lys Asn Leu Lys Ser Ser Ile Arg
1               5                   10                  15

Gln Ala Asn Leu Gly Thr Arg Pro Asn Asn Lys Lys Ser Arg Thr Arg
                20                  25                  30

Ser Thr Glu Ser His Glu Asp Arg Gln Ala Lys Val Gln Lys Ile Gln
            35                  40                  45

Ser Asp Phe Asn Leu Phe Asp Arg Gln Phe Thr Lys Arg Lys Phe Asp
    50                  55                  60

Val Gly Gly Arg Val Lys Gly Thr Glu Gly Lys Pro Gly Val Ser
65                  70                  75                  80

Arg Gly Val Gly Glu Glu Leu Arg Arg Thr Ile Gly Ala Glu Leu
                85                  90                  95

Lys Lys Arg Asn Arg Ser Gly Ala Ile Ile Asp Arg Arg Phe Gly Glu
            100                 105                 110

Asn Asn Pro His Leu Ser Val Glu Glu Lys Met Leu Glu Arg Phe Ser
        115                 120                 125

Arg Glu Gln Gln Arg Arg Ser Lys Arg Glu Leu Tyr Asn Leu Asp Ala
    130                 135                 140

Glu Asp Val Leu Thr His Gly Asn Arg Pro Leu Ser Asp Ile Asp Ser
145                 150                 155                 160

Phe Glu Glu Pro Gly Phe Gly Leu Asp Glu Gly Glu Glu Leu Asn Asp
                165                 170                 175

Glu Val Val Arg Arg Met His Phe Gly Gly Phe Glu Asp Ser Asp Ala
            180                 185                 190

Glu Asn Glu Lys Glu Gly Glu Gly Ala His Lys Ser Lys Arg Glu Val
        195                 200                 205

Met Ser Glu Ile Ile Ala Lys Ser Lys His Tyr Lys Ala Glu Arg Gln
    210                 215                 220

Ala Glu Lys Glu Arg Tyr Glu Asp Glu Arg Glu Lys Leu Asp Glu Gln
225                 230                 235                 240

Met Glu Asp Leu Gln Ser Phe Leu Ser Asp Tyr Lys Lys Ala Ser Arg
                245                 250                 255

Lys Ser Gly Ile Lys Thr Gln Arg Pro Ile Ile Ser Asp Gly Asp Ala
            260                 265                 270

Arg Tyr Asp Ser Phe Val Arg Glu Met Val Phe Asp Lys Arg Ala His
        275                 280                 285

Pro Thr Glu Arg Thr Lys Thr Glu Glu Leu Ala Gln Ile Glu Ala
    290                 295                 300

Asp Arg Leu Arg Glu Leu Glu Asp Gln Arg Ile Ser Arg Met Glu His
305                 310                 315                 320

Tyr Gln Glu Asp Ser Ala Ser Glu Ala Gly Ser Ile Glu Asp Glu Gln
                325                 330                 335
```

```
Ala Thr Asp Asn Val Phe Gly Phe Gly Lys Gly Gln Glu Asn Glu Glu
            340                 345                 350

Glu Trp Asn Gly Ile Asn Glu Glu Ala Glu Glu Ser Glu Asp Glu Glu
            355                 360                 365

Ser Val Asn Ser Asp Thr Ser Phe Val Asp Asp Glu Gln Leu Lys Val
            370                 375                 380

Glu Glu Gln Pro Leu Val Gly Ser Ala Ile Lys Asn Glu Gly Ser Glu
385                 390                 395                 400

Lys Ala Ser Leu Ala Tyr Thr Tyr Pro Cys Pro Thr Ser His Val Glu
            405                 410                 415

Phe Val Gln Leu Leu Lys Gly Leu Asp Tyr Lys Asp Tyr Pro Thr Val
            420                 425                 430

Val Ser Arg Ile Arg Thr Leu His His Val Lys Leu His Pro Asp Asn
            435                 440                 445

Lys Ser Arg Leu Glu Asn Phe Ser Val Ile Leu Leu Gln His Ile Leu
            450                 455                 460

His Leu Thr Arg Gln Pro Met Ile Ser Met Glu Leu Leu Glu His Leu
465                 470                 475                 480

Thr Glu His Leu His Ser Leu Ala Gln Gln Phe Pro Ser Ala Leu Gly
            485                 490                 495

Ile Ser Phe Ile Ser Val Val Glu Gly Met Arg Lys Arg Leu Ala Lys
            500                 505                 510

Ser Tyr Val Tyr Pro Glu Ile Lys Phe Pro Glu Ile Ser Asp Leu Leu
            515                 520                 525

Phe Phe Asn Leu Thr Gly Ser Ile Phe Pro Thr Ser Asp Lys Lys His
            530                 535                 540

Ile Val Val Ser Pro Val Met Leu Thr Met Ala Glu Ser Leu Ser Gln
545                 550                 555                 560

Ser Pro Ala Asp Ser Leu Ser Asp Val Cys Lys Lys Leu Tyr Ile Ala
            565                 570                 575

Asn Leu Phe Leu Lys Phe Gln Ser Tyr Ser His Arg Tyr Val Pro Glu
            580                 585                 590

Val Ile Thr Ala Val Ser Gln Ala Leu Tyr Leu Leu Tyr Pro Asn Phe
            595                 600                 605

Ile Ser Ile Val Pro Gly Thr Phe Ala Leu Pro Asp Ser Leu Lys Glu
            610                 615                 620

Lys Gln Asn Leu Phe Ala Ile Gln Asp Ile Ser Leu Asp Glu Pro Gln
625                 630                 635                 640

Arg Leu Ser Leu Tyr Glu Leu Glu Glu Leu Pro Thr Gly Leu Leu Gln
            645                 650                 655

Ser Ser Ile Leu Phe Ile Thr Leu Asn Leu Ile Glu Met Ala Ile Asp
            660                 665                 670

Ile Tyr Phe Lys Glu Gln Ala Phe Ile Glu Ile Phe Val Pro Ile Met
            675                 680                 685

Asp Met Leu Gln Leu Tyr Ser Leu Lys Lys Glu Leu Leu Ser Lys Arg
            690                 695                 700

Leu Ser Glu Lys Leu Leu Ser Thr Leu Gln Ala Val Ser Asp Ser Ile
705                 710                 715                 720

Glu Ser Ala Lys Ala Asn Arg Lys Pro Leu Ala Leu Gln Ser His Arg
            725                 730                 735

Pro Leu Gly Ile Thr Ser Gln Val Pro Lys Phe Glu Glu Gly Tyr Ser
            740                 745                 750
```

-continued

```
Leu Asp Lys Ser Ser His Asp Ile Asp Pro Glu Arg Ala Gln Leu Asn
            755                 760                 765
Lys Leu Arg Ala Gln His Arg Asp Ala Lys Gly Ala Ile Arg Thr
        770                 775                 780
Leu Arg Lys Asp Ala Arg Phe Ile Ala Arg Glu Arg Arg Gln Glu Gln
785                 790                 795                 800
Arg Ala Lys Asp Gln Ala Tyr Asn Glu Lys Met Arg Lys Leu Glu Asn
                805                 810                 815
Arg Leu Gln His Phe Asp Pro Ala Val
            820                 825

<210> SEQ ID NO 27
<211> LENGTH: 848
<212> TYPE: PRT
<213> ORGANISM: Caenorhabditis elegans

<400> SEQUENCE: 27

Met Gly Val Asp Lys Lys Gln Lys Gln Arg Lys Thr Asn Pro Phe Glu
1               5                   10                  15
Leu Lys Phe Asn Lys Ser Lys His Asp Ile Leu Gly Arg Lys Lys Gly
            20                  25                  30
Ala Gln Val Gly Ala Pro Thr Ala Ser Arg Lys Arg Ala His Glu Gln
        35                  40                  45
Arg Glu Gln Thr Leu Gly Val Glu Tyr Asp Arg Lys Asn Lys Ile Ser
    50                  55                  60
Lys Ile Val Asp Lys Arg Leu Gly Glu Lys Asp Gly Lys Ser Glu Glu
65                  70                  75                  80
Glu Lys Gly Ala Met Arg Phe Thr Glu Glu Arg Val Lys Asn Tyr Lys
                85                  90                  95
Arg Ala Ser Lys Phe Asn Leu Thr Asp Asp Gly Asp Glu Glu Glu Glu
            100                 105                 110
Val Leu Thr His Lys Gly Lys Ala Leu Ser Asp Ile Glu Lys Tyr Asp
        115                 120                 125
Lys Ser Met Ile Ser Asp Ser Asp Asp Glu Glu Pro Gly Asn Leu
    130                 135                 140
Gly Ser Asn Met Val Lys Val Ala His Phe Gly Gly Gly Glu Lys Thr
145                 150                 155                 160
Ala Glu Glu His Val Arg Glu Lys Ile Ser Arg Glu Asp Met Ile Ser
                165                 170                 175
Asn Leu Ile Ala Lys Thr Lys Leu Ala Arg His Glu Lys Gln Gln Gln
            180                 185                 190
Lys Asp Glu Leu Glu Leu Met Thr Glu Ser Leu Asp Ser Lys Tyr Gln
        195                 200                 205
Ala Leu Met Gly Lys Met Lys Ala Ser Phe Arg Pro Thr Gly Arg Gln
    210                 215                 220
Pro Leu Glu Lys Asp Asp Tyr Asp Lys Leu Thr Ile Thr Leu Lys Thr
225                 230                 235                 240
Glu Ala Asp Ala Arg Ala Thr Pro Ala Asp Arg Lys Leu Ser Glu Glu
                245                 250                 255
Glu Glu Ala Leu Lys Glu Lys Glu Arg Leu Glu Thr Leu Glu Ala Ala
            260                 265                 270
Pro Asp Ala Asp Val Asp Ile Asp Ala Gly Ser Lys Ala Asp Ala Arg
        275                 280                 285
Lys Val Gln Ala Lys Asn Ser Arg Phe Glu Val Lys Phe Asp Asp Glu
    290                 295                 300
```

-continued

```
Gly Gly Leu Ile Asp Glu Asp Thr Val Glu Lys Ser Arg Ile Leu Lys
305                 310                 315                 320
Lys Asn Leu Asp Gly Ser Asp Glu Ser Asp Asp Asp Glu Asp Leu Glu
                325                 330                 335
Asp Glu Glu Glu Asp Leu Asp Asp Leu Leu Glu Asp Glu Asp Glu Leu
            340                 345                 350
Glu Glu Asp Ser Asp Asp Glu Glu Ala Gln Glu Ala Gln Lys Val Val
            355                 360                 365
Lys Lys Ala Lys Lys Ser Ala Pro Glu Pro Ala Glu Thr Leu Pro Phe
370                 375                 380
Val Phe Glu Met Pro Lys Asn Tyr Lys Lys Phe Cys Ala Leu Leu Glu
385                 390                 395                 400
Lys His Ser Glu Ser Met Asp Leu Val Leu Glu Arg Leu Val Lys Cys
                405                 410                 415
His His Pro Ser Leu Lys Glu Gly Asn Lys Lys Arg Leu Asn Lys Leu
            420                 425                 430
Phe Leu Leu Cys Leu Arg Trp Phe Asp Asp Met Ser Lys Glu Glu Leu
            435                 440                 445
Thr Ala Glu Ser Val Lys Glu Met Asn Leu Ala Gln Glu Thr Met His
            450                 455                 460
Ala Leu Met Lys Phe Asp Ile Gln Tyr Gly Val Arg Cys Val Arg Ala
465                 470                 475                 480
Leu Ile Arg Gln His Trp Lys Gly Arg Gln Asp Lys Gln Lys Ser Ser
                485                 490                 495
Pro Val Ser Phe Gly Leu Ile Ser Ala Ile Arg Leu Val Ser Gly Leu
            500                 505                 510
Phe Pro Val Ala Asp Ser Trp His Pro Val Val Val Pro Ala Leu Phe
            515                 520                 525
Leu Ala Thr Glu Ala Leu Cys Ser Ala Lys Cys Ala Asn Leu Asn Ala
            530                 535                 540
Leu Ala Lys Gln Ile Gln Leu Ala Asn Ala Ile Val Glu Tyr Val Ser
545                 550                 555                 560
Glu Ser Lys Arg Tyr Val Pro Glu Leu Val Ala Phe Ala Arg Ser Ala
                565                 570                 575
Leu Leu Leu Ala Val Thr Glu Lys Ser Glu Lys Phe Ala Thr Asn Gly
            580                 585                 590
Phe Pro Ile Ser Lys Pro His Thr Glu Met Leu Cys Phe Glu Glu Lys
            595                 600                 605
Leu Leu Phe Leu Thr Lys Asn Tyr Asn Trp Ile Ser Gln Lys Glu Phe
            610                 615                 620
Asp Leu Ser Ser Phe Asn Arg Tyr Ile Asp Glu Leu Tyr Leu Lys Met
625                 630                 635                 640
Thr Arg Lys Tyr Thr Gly Pro Ala Leu Gln Pro Ile Ser Leu Thr Thr
                645                 650                 655
Ile Phe Asn Asn Ser Pro Ser Asp Pro Ser Leu Lys Leu His Val Leu
            660                 665                 670
Arg Ala Leu Leu Ser Leu Ile Gln His Leu Arg Val Ile Tyr Ser Asn
            675                 680                 685
Gln Asn Glu Thr Tyr Ser Ile Val Phe Lys Pro Phe Leu Arg Ile Leu
            690                 695                 700
Glu Ser Ile Gln Ala Lys Asn Leu Pro Ala Glu Val Gln Glu Glu Leu
705                 710                 715                 720
```

-continued

Glu Thr Leu Cys Ala Ser Met Lys Ala Glu Ile Gly Ala Lys Cys Arg
                    725                 730                 735

Leu Val His Leu Ser Leu Val Lys Thr Glu Lys Ser Met Leu Lys Met
                740                 745                 750

Leu Glu Pro Arg Phe Glu Trp Asp Phe Asp Pro Glu Arg Pro His His
            755                 760                 765

Gly Pro Lys Asp Glu Lys Lys Leu Thr Lys Asn Leu Arg Asn Glu
        770                 775                 780

Arg Arg Gly Ala Ile Lys Glu Leu Arg Lys Asp Thr Ala Phe Leu Ala
785                 790                 795                 800

Arg Lys Gln Leu Ser Ser Val Lys Thr Lys Asp Arg Ala Arg Ile Ala
                805                 810                 815

Ala Thr Lys Arg Val Met Gly Gly Leu Met Gln Gln Gly Glu Trp
                820                 825                 830

Asn Lys Glu Lys Arg Thr Ala Asp Val Glu Lys Lys Asp Lys Lys
            835                 840                 845

<210> SEQ ID NO 28
<211> LENGTH: 873
<212> TYPE: PRT
<213> ORGANISM: Homo sapiens

<400> SEQUENCE: 28

Leu Ser Leu Phe Gly Ser Arg Ala Leu Gly Arg Ser Gly Ala Arg Ala
1               5                   10                  15

Met Ala Lys Ala Lys Val Gly Ala Arg Arg Lys Ala Ser Gly Ala
            20                  25                  30

Pro Ala Gly Ala Arg Gly Gly Pro Ala Lys Ala Asn Ser Asn Pro Phe
        35                  40                  45

Glu Val Lys Val Asn Arg Gln Lys Phe Gln Ile Leu Gly Arg Lys Thr
    50                  55                  60

Arg His Asp Val Gly Leu Pro Gly Val Ser Arg Ala Arg Ala Leu Arg
65                  70                  75                  80

Lys Arg Thr Gln Thr Leu Leu Lys Glu Tyr Lys Glu Arg Asp Lys Ser
                85                  90                  95

Asn Val Phe Arg Asp Lys Arg Phe Gly Glu Tyr Asn Ser Asn Met Ser
            100                 105                 110

Pro Glu Glu Lys Met Met Lys Arg Phe Ala Leu Glu Gln Gln Arg His
        115                 120                 125

His Glu Lys Lys Ser Ile Tyr Asn Leu Asn Glu Asp Glu Leu Thr
    130                 135                 140

His Tyr Gly Gln Ser Leu Ala Asp Ile Leu Lys His Asn Asp Ile Val
145                 150                 155                 160

Asp Ser Asp Ser Asp Ala Glu Asp Arg Gly Thr Leu Ser Ala Glu Leu
                165                 170                 175

Thr Ala Ala His Phe Gly Gly Gly Gly Leu Leu His Lys Lys Thr
            180                 185                 190

Gln Gln Glu Gly Glu Glu Arg Glu Lys Pro Lys Ser Arg Lys Glu Leu
        195                 200                 205

Ile Glu Glu Leu Ile Ala Lys Ser Lys Gln Glu Lys Arg Glu Arg Gln
    210                 215                 220

Ala Gln Arg Glu Asp Ala Leu Glu Leu Thr Glu Lys Leu Asp Gln Asp
225                 230                 235                 240

Trp Lys Glu Ile Gln Thr Leu Leu Ser His Lys Thr Pro Lys Ser Glu
                245                 250                 255

```
Asn Arg Asp Lys Lys Glu Lys Pro Lys Pro Ala Tyr Asp Met Met
            260                 265                 270

Val Arg Glu Leu Gly Phe Glu Met Lys Ala Gln Pro Ser Asn Arg Met
            275                 280                 285

Lys Thr Glu Ala Glu Leu Ala Lys Glu Glu Gln Glu His Leu Arg Lys
            290                 295                 300

Leu Glu Ala Glu Arg Leu Arg Arg Met Leu Gly Lys Asp Glu Asp Glu
305                 310                 315                 320

Asn Val Lys Lys Pro Lys His Met Ser Ala Asp Asp Leu Asn Asp Gly
                325                 330                 335

Phe Val Leu Asp Lys Asp Arg Arg Leu Leu Ser Tyr Lys Asp Gly
            340                 345                 350

Lys Met Asn Val Glu Glu Asp Val Gln Glu Glu Gln Ser Lys Glu Ala
            355                 360                 365

Ser Asp Pro Glu Ser Asn Glu Glu Gly Asp Ser Ser Gly Gly Glu
370                 375                 380

Asp Thr Glu Glu Ser Asp Ser Pro Asp Ser His Leu Asp Leu Glu Ser
385                 390                 395                 400

Asn Val Glu Ser Glu Glu Glu Asn Glu Lys Pro Ala Lys Glu Gln Arg
            405                 410                 415

Gln Thr Pro Gly Lys Gly Leu Ile Ser Gly Lys Glu Arg Ala Gly Lys
            420                 425                 430

Ala Thr Arg Asp Glu Leu Pro Tyr Thr Phe Ala Ala Pro Glu Ser Tyr
            435                 440                 445

Glu Glu Leu Arg Ser Leu Leu Leu Gly Arg Ser Met Glu Glu Gln Leu
            450                 455                 460

Leu Val Val Glu Arg Ile Gln Lys Cys Asn His Pro Ser Leu Ala Glu
465                 470                 475                 480

Gly Asn Lys Ala Lys Leu Glu Lys Leu Phe Gly Phe Leu Leu Glu Tyr
            485                 490                 495

Val Gly Asp Leu Ala Thr Asp Asp Pro Pro Asp Leu Thr Val Ile Asp
            500                 505                 510

Lys Leu Val Val His Leu Tyr His Leu Cys Gln Met Phe Pro Glu Ser
            515                 520                 525

Ala Ser Asp Ala Ile Lys Phe Val Leu Arg Asp Ala Met His Glu Met
530                 535                 540

Glu Glu Met Ile Glu Thr Lys Gly Arg Ala Ala Leu Pro Gly Leu Asp
545                 550                 555                 560

Val Leu Ile Tyr Leu Lys Ile Thr Gly Leu Leu Phe Pro Thr Ser Asp
            565                 570                 575

Phe Trp His Pro Val Val Thr Pro Ala Leu Val Cys Leu Ser Gln Leu
            580                 585                 590

Leu Thr Lys Cys Pro Ile Leu Ser Leu Gln Asp Val Val Lys Gly Leu
            595                 600                 605

Phe Val Cys Cys Leu Phe Leu Glu Tyr Val Ala Leu Ser Gln Arg Phe
            610                 615                 620

Ile Pro Glu Leu Ile Asn Phe Leu Leu Gly Ile Leu Tyr Ile Ala Thr
625                 630                 635                 640

Pro Asn Lys Ala Ser Gln Gly Ser Thr Leu Val His Pro Phe Arg Ala
                645                 650                 655

Leu Gly Lys Asn Ser Glu Leu Leu Val Val Ser Ala Arg Glu Asp Val
            660                 665                 670
```

-continued

```
Ala Thr Trp Gln Gln Ser Ser Leu Ser Leu Arg Trp Ala Ser Arg Leu
            675                 680                 685

Arg Ala Pro Thr Ser Thr Glu Ala Asn His Ile Arg Leu Ser Cys Leu
            690                 695                 700

Ala Val Gly Leu Ala Leu Leu Lys Arg Cys Val Leu Met Tyr Gly Ser
705                 710                 715                 720

Leu Pro Ser Phe His Ala Ile Met Gly Pro Leu Gln Ala Leu Leu Thr
                725                 730                 735

Asp His Leu Ala Asp Cys Ser His Pro Gln Glu Leu Gln Glu Leu Cys
                740                 745                 750

Gln Ser Thr Leu Thr Glu Met Glu Ser Gln Lys Gln Leu Cys Arg Pro
            755                 760                 765

Leu Thr Cys Glu Lys Ser Lys Pro Val Pro Leu Lys Leu Phe Thr Pro
        770                 775                 780

Arg Leu Val Lys Val Leu Glu Phe Gly Arg Lys Gln Gly Ser Ser Lys
785                 790                 795                 800

Glu Glu Gln Glu Arg Lys Arg Leu Ile His Lys His Lys Arg Glu Phe
                805                 810                 815

Lys Gly Ala Val Arg Glu Ile Arg Lys Asp Asn Gln Phe Leu Ala Arg
                820                 825                 830

Met Gln Leu Ser Glu Ile Met Glu Arg Asp Ala Glu Arg Lys Arg Lys
            835                 840                 845

Val Lys Gln Leu Phe Asn Ser Leu Ala Thr Gln Glu Gly Glu Trp Lys
    850                 855                 860

Ala Leu Lys Arg Lys Lys Phe Lys Lys
865                 870
```

YEAST MAMMALIAN REGULATORS OF CELL PROLIFERATION

This application claims the benefits of provisional application No. 60/127,226, filed Mar. 31, 1999.

This invention was made in part with government support under grants GM18858 and GM59911 from the National Institutes of Health. The government has certain rights in the invention.

FIELD OF THE INVENTION

This invention generally relates to a novel cell cycle regulatory gene named Essential for Mitotic Growth 1 (Emg1) that is conserved in yeast, worms, mammals and plants. Additionally, this invention relates to a temperature sensitive mutation of Emg1, designated Emg1-1. Also, this invention relates to an Emg1 interactive protein, designated Emg-1-nuclear interacting protein-1 (ENIP1), and the respective coding sequence. Furthermore, this invention relates to cells and organisms that are made deficient in expression or made to over express these genes or proteins. Further still, drugs screens for compounds that are agonistic or antagonistic to Emg1, Emg1-1 and ENIP1 regulation of the cell cycle are claimed by this invention. Even further still, screens for Emg1, Emg1-1 and ENIP1 intra- and interspecific homologs as well as associated binding molecules are claimed by this invention.

BACKGROUND

In order for cells to proliferate and divide faithfully, cellular mechanisms have evolved to ensure proper progression through the eukaryotic cell division cycle. Expression of genes encoding proteins that promote passage through the cell cycle are tightly regulated and carefully coordinated to physiological and environmental cues such as growth promoting stimuli and growth arresting signals. Progression through the cell cycle requires the ordered synthesis, assembly and movement of macromolecular cell structures including proteins, membranes, and importantly, the genetic information encoded by the genomic DNA. Coordination of these processes involves the successive activation of specific regulatory cell cycle proteins known as cyclins and cyclin-dependent kinases which in turn orchestrate the transcription of genes whose products effect defined cellular programs for cell division. In addition to signals that promote progression, the cell cycle is also regulated by negative controls which prevent cell proliferation during circumstances in which damage to, or instability of, the genome is sensed. These surveillance systems, called checkpoints, prevent passage through the cell cycle until the cellular damage can be repaired; or in the event of irreparable damage, permanently stall cell growth and, in some cells, trigger the programmed cell death pathway. A different, programmed exit from the cell cycle, such as the process of terminal differentiation by specialized cells, also requires a coordinated response to specific physiological cues and activation of transcriptional events which lead to the cessation of proliferation. Thus cellular growth must balance positive and negative controls on cell cycle progression in order to ensure the replication of genetic material with high fidelity as well as the maintenance of cell-specific phenotypes.

The tight control over cell proliferation by both positive and negative regulators indicates the central importance of coordinating cellular proliferation with respect to physiological and environmental stimuli. The loss of this control, through genetic mutation of key regulatory components of the cell cycle or impaired sensing of external cues can lead to deregulated growth and disease states with devastating consequences for the cell, tissue and organism. One example is the progression from normal cells to cancer cells which is thought to require a number of genetic changes in proteins that normally control the cell cycle. Several lines of evidence including basic research in model systems such as yeast, correlations with the frequencies of mutation in growth regulatory genes from tumor biopsies, studies on tumor-causing viruses, and identification of the molecular basis for genetic predisposition to tumor development in patients with hereditary diseases have pointed to common molecular and genetic mechanisms which facilitate the evolution of cancer cells. Specifically, mutations that lead to decreased fidelity in the replication and repair of the genome, such as in genes that regulate cell cycle checkpoints, the activity of the cyclin and cyclin-dependent kinases, or transcription factors that coordinate cell cycle progression, are common means by which a cells lose genetic stability. Loss of genetic stability is a hallmark of tumor cells. Conversely, understanding the mechanisms by which cells can re-enter the cell cycle from a resting state, such as a terminally differentiated cell type, should provide targets for pro-proliferative therapies in cases where cellular growth is needed to repair tissue injury, such as in response to ischemic damage to the heart or liver regeneration or regeneration of nervous tissues, such as in Alzheimer's disease.

Therefore, what is needed is the identification of key regulatory genes that control cell proliferation as they may provide a means for the screening of compounds that are agonistic or antagonistic for mitosis. Such compounds, once identified, may be useful as diagnostic or therapeutic agents in the treatment of diseases characterized by unregulated cell growth.

SUMMARY OF THE INVENTION

The present invention generally comprises a novel, substantially purified oligonucleotide sequences from *S. cerevisiae,* mouse and human that encode for the newly discovered genes, Emg1, Emg1-1 and ENIP1. The expression of Emg1 and ENIP1 have been shown to be required for mitosis. The gene is highly conserved. For example, transfection of murine Emg1 into yeast expressing a vector containing a temperature sensitive loss of function (lof) Emg1 mutant (e.g., Emg1-1) overcomes the deficiency of the mutant. Additionally, for example, transfection of a vector expressing murine Emg1 into yeast harboring a null allele of Emg1 overcomes the growth deficiency of the yeast mutant. Mouse Emg1 is 50% homologous with yeast Emg1. Mouse and human Emg1 share 87% homology.

The present invention generally relates to compositions and methods of identifying and testing Emg1 pathway agonists and antagonists. The present invention is not limited by the method of the employed screen. In one embodiment, the present invention contemplates screening suspected compounds in a system utilizing transfected cell lines. In one embodiment, the cells may be transfected transiently. In another embodiment, the cells may be stably transfected. In yet another embodiment, translation products of the invention may be used in a cell-free assay system. Furthermore, in yet another embodiment, antibodies generated to the translation products of the invention may be used in immunoprecipitation assays. In still another embodiment yeast based assays incorporating transfected yeast (e.g., transiently or stability transfected yeast) may be used to screen for Emg1 agonists and antagonists. And in still another embodiment, transgenic animals may be generated with the transgene contained in a vector containing an inducible, tissue specific promotor or a restrictive promoter such as a temperature sensitive promoter. In still yet another embodiment, the vector may contain a temperature sensitive variant of Emg1, for example Emg1-1.

The invention also relates to methods to identify other members of the Emg1 pathway (e.g., binding partners). One such binding partner has already been identified as the Emg1-nuclear interacting protein-1 (ENIP1). ENIP1 is essential for cell growth. The present invention is not limited to the methods employed to identify Emg1 pathway constituents. In one embodiment, antibodies generated to translation products of the invention may be used in immunoprecipitation experiments to isolate novel Emg1 pathway constituents or natural mutations thereof. In another embodiment, the invention may be used to generate fusion proteins (e.g., Emg1-GST fusion proteins) that could also be used to isolate novel Emg1, Emg1-1 and ENIP1 pathway constituents or natural mutations thereof. In yet another embodiment, screens may be conducted using the yeast two-hybrid system using Emg1 as the bait. In yet another embodiment, screens may be conducted using affinity chromatography using Emg1 as the ligand.

The invention also relates to the production of derivatives of the Emg1, Emg1-1 and ENIP1 genes such as, but not limited to, mutated gene sequences (and portions thereof), transcription and translation products (and portions thereof), expression constructs, transfected cells and transgenic animals generated from the nucleotide sequences (and portions thereof). The present invention also contemplates antibodies (both polyclonal and monoclonal) to the gene product or nucleic acid aptamers, including the product of mutated genes.

The present invention contemplates using oligonucleotide probes that are complementary to a portion of the Emg1, Emg1-1 or ENIP1 gene sequences (e.g., the human gene sequence) to detect the presence of the Emg1, Emg1-1 or ENIP1 DNA or RNA, respectively. Such probes can be complementary to a highly conserved region of the gene, i.e., a portion of the gene which is in common between yeast and humans. Examples of probes to such conserved regions of Emg1 and Emg1-1 are provided in FIG. 8. On the other hand, the present invention also contemplates probes complementary to less conserved regions or even unique regions (e.g., a portion of the gene having a sequence unique to the human gene). Of course, such probes can also have non-complementary portions (e.g., portions useful for detection or isolation).

In addition, the present invention contemplates a diagnostic wherein, for example, a sample of the DNA (e.g., human DNA), of the Emg1, Emg1-1 or ENIP1 gene sequence is determined (e.g., by sequencing) to identify suspected mutations. In such a method, the present invention contemplates isolating the gene from a mixture of DNA. Such isolation can be done using one or more of the probes described above. For example, the present invention contemplates utilizing oligonucleotides that are complementary to the gene as primers in PCR (see U.S. Pat. Nos. 4,683,195, 4,683,202 and 4,965,188, all of which are hereby incorporated by reference). Such primers can be complementary to internal regions of the gene (such as the oligonucleotides in FIG. 8). More preferably, primers can be designed that will hybridize to each end of the gene so that the entire gene can be amplified and analyzed (e.g., for mutations).

The present invention also relates to the identification of new homologs of Emg1, Emg1-1 or ENIP1 or natural mutations thereof. The present invention is not limited to a particular method to identify Emg1, Emg1-1 or ENIP1 homologs. The present invention contemplates screening for homologs using a variety of molecular procedures. In one embodiment, screens are conducted using Northern and Southern blotting. In another embodiment, screens are conducted using DNA chip arrays composed of Emg1, Emg1-1 or ENIP1 DNA sequences for binding complementary sequences (again the oligonucleotides in FIG. 8 are illustrative of oligonucleotides which might be employed in such screens for new homologs). The invention contemplates methods for screening for intra- and inter-specific homologs of Emg1, Emg1-1 or ENIP1, one method comprising (for example): a) providing in any order: i) extracts from cell suspected of containing said homolog, ii) antibodies reactive to Emg1 and specific for at least a portion of the peptide of Emg1; and b) mixing said antibody with said extract under conditions such that said homolog is detected. The present invention further contemplates a method to screen for homologs of Emg1 comprising: a) extracts from cells suspected of containing said homolog; b) contacting the extract with anti-Emg1; c) detecting said homolog by techniques known to those practiced in the art, for example Western blotting.

The invention also contemplates novel compositions such as the Emg1, Emg1-1 or ENIP1 gene sequence (or portions thereof) inserted into a transfection vector. The invention is not limited to a particular transfection vector. The present invention also contemplates a composition comprising said transfection vector transfected into primary cells, a cell line (e.g., mammalian or yeast cells) or embryonic cells. The invention is not limited to a particular cell line, cell type or to the species from which the cells are derived. Another contemplated composition comprises the Emg1, Emg1-1 or ENIP1 gene sequence in an appropriate vector used to make a transgenic animal. Such Emg1, Emg1-1 or ENIP1 gene sequences may be mutated such that they are loss of function (lof) or gain of function (gof) mutants or may be combined with other gene sequences (the secondary gene sequence) for the purposes of producing a fusion product. The invention is not limited to any specific secondary gene sequence. The secondary gene sequence may be used to permit, for example, the isolation of the gene, the isolation of transcription product or the isolation of translation product. Likewise, said secondary sequence may serve as a marker for identifying or visualizing the vector, the translated RNA or the transcribed protein.

Furthermore, the present invention also contemplates using the above-named sequences and derived products in screening assays. The invention is not limited to any particular screening method. In one embodiment, the invention contemplates drug screens for compounds that are agonistic or antagonistic for Emg1, Emg1-1 or ENIP1 function. In one embodiment, cells (e.g., mammalian or yeast) are transfected with vectors containing either a lof mutant of Emg1, a human Emg1 gene or a yeast Emg1 gene or a complementary DNA (cDNA). Additionally, expression vectors containing Emg1-1 or ENIP1 genes, or lof mutants, may be used. In another embodiment, instead of using Emg1 lof of function mutants, yeast cells are made defective in Emg1, Emg1-1 or ENIP1 expression through homologous recombination. In one embodiment, the expression vectors are under the control of temperature sensitive promoters or vectors expressing Emg1-1, for example, are used. Cells can be exposed to the compound suspected of altering Emg1 or ENIP1 function. The culture temperature can be raised to the restrictive temperature and inhibition or enhancement of mitosis can be measured by techniques known to those practiced in the art. The invention is not limited to any particular measurement technique. Various methods are envisioned. For example, mitosis could be measured by use of fluorescent dyes that intercalate into DNA, by the measurement of $H^3$-thymidine incorporation or by colormetric assays. Such assays would permit the use of high throughput screening methods.

The present invention specifically contemplates that both anti-cancer drugs and antibiotics can be discovered using compound screening assays which employ either the Emg1, Emg1-1 or ENIP1 gene or the corresponding gene products. For antibiotics, use of both the yeast gene (and corresponding gene products) along with the human gene (and corresponding gene products) permits a screening assay to identify compounds that interface with yeast (and fungal) cell growth, and yet do not interface with human cell growth. Emg1 sequence homologs have been discovered in rice. Thus, the invention contemplates that herbicides can be discovered using compound screening assays which employ either the Emg1, Emg1-1 or ENIP1 gene or corresponding gene products.

In one embodiment, the present invention contemplates a composition comprising isolated and purified DNA having an oligonucleotide sequence selected from the group consisting of SEQ ID NO: 6, SEQ ID NO: 8, SEQ ID NO: 10, SEQ ID NO: 16, SEQ ID NO: 23, and SEQ ID NO: 24. The present invention further contemplates a composition comprising RNA transcribed from such DNA as well as a composition comprising protein translated from transcribed RNA. The protein (or portion thereof) can be used as an antigen and the present invention specifically contemplates an antibody produced from the protein.

The present invention contemplates that the isolated and purified DNA (i.e., having an oligonucleotide sequence selected from the group consisting of SEQ ID NO: 6, SEQ ID NO: 8, SEQ ID NO: 10, SEQ ID NO: 16, SEQ ID NO: 23, and SEQ ID NO: 24) can be used to make transgenic organisms. For example, the present invention contemplates both transgenic animals comprising such DNA sequences as well as transgenic microorganisms (e.g., fungus) comprising such DNA sequences. Such transgeneic animals and microorganisms will typically be made using such DNA sequences in operable combination with promoters and enhancers in a vector. The present invention also contemplates such vectors and expression constructs comprising such DNA sequences.

While a variety of screening methods are contemplated, in one embodiment, the present invention contemplates a method to detect Emg1 agonists and antagonists, comprising: a) providing i) one or more compounds suspected of modulating Emg1 activity, ii) a first yeast cell line comprising the yeast Emg1 gene; ii) a second yeast cell line transfected with the human Emg1 gene so as to create a transfected yeast cell line; b) contacting a portion of said cells from i) said first yeast cell line and ii) said transfected yeast cell line, with said one or more compounds under conditions such that said compound can enter said cells, so as to create treated portions and untreated portions of cells; and c) comparing the amount of cell division of said treated cells with the amount of cell division of said untreated cells.

The present invention also comtemplates isolated and purified amino acids sequences selected from the group consisting of SEQ ID NO: 7, SEQ ID NO: 9, SEQ ID NO: 11, SEQ ID NO: 17, SEQ ID NO: 25, SEQ ID NO: 26, SEQ ID NO: 27 and SEQ ID NO: 28.

The present invention also contemplates an assay to detect agonists and antagonists to the binding of Emg1 with ENIP1, comprising: a) providing i) Emg1; ii) ENIP1: iii) one or more compounds suspected of modulating Emg1/ENIP1 binding interaction; b) mixing said Emg1, said ENIP1 and said one or more compounds to produce a test mixture; c) detecting binding of said Emg1 and said ENIP1 to each other in said test mixture. Alternatively, step c) can involve the measurement of unbound Emg1 or ENIP1. In other words, the extent to which the added compound disrupts or promotes binding can be measured. Measuring can be by a variety of methods (e.g., coprecipitation, Western blotting, etc.).

DESCRIPTION OF THE FIGURES

FIG. 2 shows the amino acid alignment of *S. cerevisiae* Emg1 (SEQ ID NO:1) with homologues from *S. pombe* (SEQ ID NO:2), *C. elegans* (SEQ ID NO:3), mouse (SEQ ID NO:4) and human (SEQ ID NO:5) identified by computer-aided searching of existing sequence databases.

FIG. 4, panel B depicts a blot analysis of the distribution of Emg1 mRNA in mouse tissues.

FIG. 5 shows the DNA sequence of Emg1 from human (SEQ ID NO:6) and its encoded protein (SEQ ID NO:7).

FIG. 6 shows the DNA sequence of Emg1 from *S. cerevisiae* (SEQ ID NO:8) and its encoded protein (SEQ ID NO:9).

FIG. 7 shows the DNA sequence of Emg1 from mouse (SEQ ID NO:10) and its encoded protein (SEQ ID NO:11).

FIG. 8 shows examples of DNA sequences complementary to regions of Emg1 DNA homologous between the sequences of FIGS. 5–7. Such sequences may be use as binding probes to isolate DNA encoding Emg1 homologs (SEQ ID NO:12; SEQ ID NO:13; SEQ ID NO:14; SEQ ID NO:15).

FIG. 9 shows the nucleotide (SEQ ID NO:16) and amino acid (SEQ ID NO:17) sequences for Drosophila Emg1.

FIG. 10A shows sequence segments encompassing the point mutations of Emg1-1.

FIG. 12 shows the nucleic acid sequence of human ENIP1 (SEQ ID NO:23).

FIG. 13 shows the nucleic acid sequence of yeast ENIP1 (SEQ ID NO:24).

FIGS. 14A and 14B show the amino acid sequences of yeast, *C. elegans* and human ENIP1 (SEQ ID NOS:25–28).

DEFINITIONS

Figure 1:
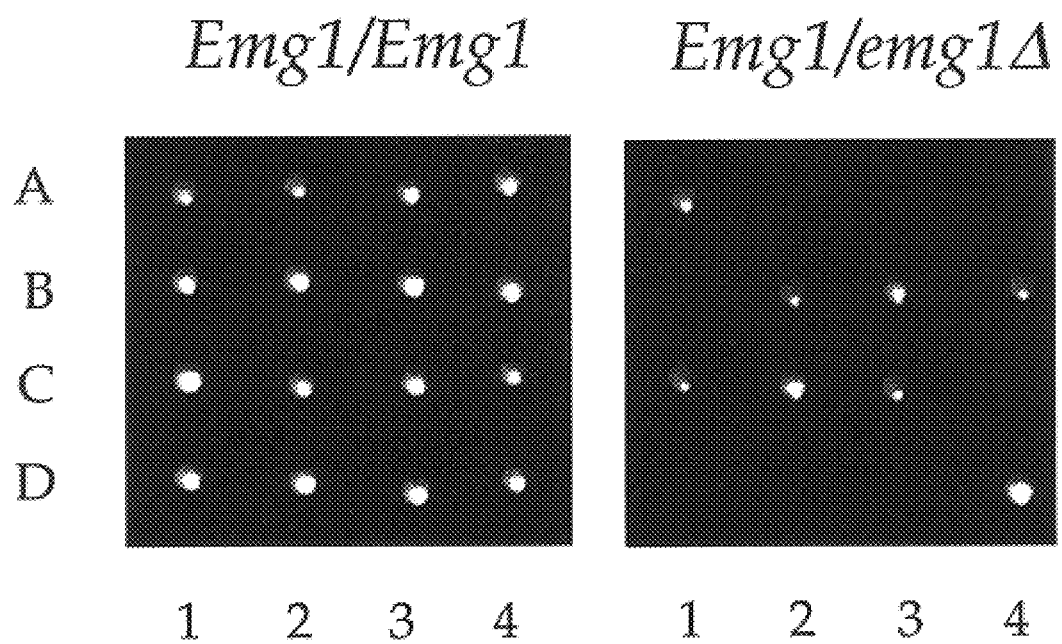
FIG. 1 shows comparison of diploid wild type yeast and heterozygous diploid yeast.

To facilitate understanding of the invention, a number of terms are defined below.

The term "binding interaction" when used in relation to proteins shall be defined as the ability of two or more proteins to bind to each other (e.g., to produce an aggregate). The present invention makes no limit on the stringency of the binding interaction so long as the interaction can be detected by methods known to those practiced in the art (e.g., by Western blot, coimmunoprecipitation, spectrophotometry, colormetric assay, etc.).

The term "homology" when used in relation to proteins refers to a degree of complementarity. There may be partial homology or complete homology (i.e., identity). A partially complementary sequence is one that at least partially inhibits a completely complementary sequence from performing its function (e.g., enzymatic, binding, etc) in vivo or in vitro and is referred to using the functional term "substantially homologous." The inhibition function of the completely complementary sequence may be examined using an enzymatic assay, a binding assay or other assay designed to measure the particular function of the completely complementary protein. A substantially homologous sequence or probe will compete for and inhibit the function (e.g., the binding or enzymatic function) of a sequence which is completely homologous to a target under conditions of low stringency. This is not to say that conditions of low stringency are such that non-specific interaction is permitted; low stringency conditions require that the interaction of the sequence with its substrate be a specific (i.e., selective) interaction. The absence of non-specific binding may be tested by the use of a second target which lacks even a partial degree of complementarity (e.g., less than about 30% identity); in the absence of non-specific interaction the probe will not react to the second non-complementary target.

The term "evolutionary homology" refers to structures or sequences in different organisms having fundamental similarity because of their having descended from a common ancestor. Human Emg1 is termed homologous to yeast Emg1 because of a significant degree of sequence identity.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

As used herein, the term "fusion protein" refers to a chimeric protein containing the protein of interest (i.e., Emg1 and fragments thereof) joined to an exogenous protein fragment (the fusion partner which consists of a non-Emg1 sequence). The fusion partner may provide a detectable moiety, may provide an affinity tag to allow purification of the recombinant fusion protein from the host cell, or both. If desired, the fusion protein may be removed from the protein of interest by a variety of enzymatic or chemical means known to the art.

As used herein, the term "purified" or "to purify" refers to the removal of contaminants from a sample. The present invention contemplates purified compositions (discussed above).

As used herein, the term "substantially purified" refers to the removal of a significant portion of the contaminants of a sample to the extent that the substance of interest is recognizable by techniques known to those skilled in the art as the most abundant substance in the mixture.

As used herein the term "portion" when in reference to a protein (as in "a portion of a given protein") refers to fragments of that protein. The fragments may range in size from four amino acid residues to the entire amino acid sequence minus one amino acid. In one embodiment, the present invention contemplates "functional portions" of a protein. Such portions are "functional" if they contain a binding region (i.e., a region having affinity for another molecule) and such binding can take place (i.e., the binding region functions, albeit with perhaps lower affinity than that observed for the full-length protein). Such "functional proteins" of the Emg1 gene product are typically greater than 50 amino acids in length, and more typically greater than 100 amino acids in length. "Functional portions" may also be "conserved portions" of the protein. The alignment of the yeast and human gene products (described herein) permit one skilled in the art to select conserved portions of the protein (i.e., those portions in common between yeast and man) as well as unconserved portions (i.e., those portions unique to either yeast or man). The present invention contemplates conserved portions 20 amino acids in length or greater, and more typically greater than 50 amino acids in length.

As used herein the term "portion" when in reference to an oligonucleotide sequence (as in "a portion of a given sequence") refers to fragments of that sequence. The fragments may range in size from four base residues to the entire oligonucleotide sequence minus one base. More typically, such portions are 15 nucleotides in length or greater. Again, such portions may be conserved portions (see FIG. 8). On the other hand, such portions may be unique portions of the gene.

"Staining" shall be defined as any number of processes known to those in the field that are used to better visualize, distinguish or identify a specific component(s) and/or feature(s) of a cell or cells.

"Immunofluorescence" is a staining technique used to identify, mark, label, visualize or make readily apparent by procedures known to those practiced in the art, where a ligand (usually an antibody) is bound to a receptor (usually an antigen) and such ligand, if an antibody, is conjugated to a fluorescent molecule, or the ligand is then bound by an antibody specific for the ligand, and said antibody is conjugated to a fluorescent molecule, where said fluorescent molecule can be visualized with the appropriate instrument (e.g., a fluorescent microscope).

"Antibody" shall be defined as a glycoprotein produced by B cells that binds with high specificity to the agent (usually, but not always, a peptide), or a structurally similar agent, that generated its production. Antibodies may be produced by any of the known methodologies [Current Protocols in Immunology (1998) John Wiley and Sons, Inc., N.Y.] and may be either polyclonal or monoclonal.

"Loss of function" (lof) shall be defined as all modifications (e.g., deletions, substitutions, additions, etc.) to an oligonucleotide that, when that oligonucleotide is transfected into a host organism and translated into a peptide, that peptide will function with decreased efficiency as compared to the wild type peptide when the gene or gene product is induced to function whether that induction be continuous or non-continuous. It may, in effect, function as a diminisher of natural gene function if the natural gene is present and functional in the host into which the lof oligonucleotide was transfected, or may negatively interfere with processes in the host if the natural gene is not present or is non-functional.

"In operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

"Heterologous DNA" sequence refers to a nucleotide sequence which is not endogenous to the cell into which it is introduced. Heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell into which it is introduced and which contains some modification relative to the naturally-occurring sequence. An example of heterologous DNA of the present invention comprises the Emg1 human DNA sequence introduced into yeast.

"Gain of function" (gof) shall be defined as all modifications (e.g., deletions, substitutions, additions, etc.) to an oligonucleotide that, when that oligonucleotide is transfected into a host organism and translated into a peptide, that peptide will function with increased efficiency as compared to the wild type peptide when the gene or gene product is induced to function whether that induction be continuous or non-continuous. It may, in effect, function as an augmenter of the natural gene if the natural gene is present and functional in the host into which the gof oligonucleotide was transfected, or it may add that function to the host if the natural gene is not present or is non-functional.

"Antigen" shall be defined as a protein, glycoprotein, lipoprotein, lipid or other substance that is reactive with an antibody specific for a portion of the molecule.

The terms "immunoprecipitate", "immunoprecipitated", "immunoprecipitation" refer to the use of antibody to take an antigen out of solution by precipitation.

The term "affinity purification" refers to the use of an antibody to separate its antigen or a portion thereof from a mixture of other molecules because of affinity for the antigen.

"Morphology" shall be defined as the visual appearance of a cell or organism when viewed with the eye, a light microscope, a confocal microscope or an electron-microscope, as appropriate.

"Patient" shall be defined as a human or other animal, such as a guinea pig or mouse and the like, capable of having cell cycle (influenced) determined diseases, either naturally occurring or induced, including but not limited to cancer.

GENERAL DESCRIPTION OF THE INVENTION

A. Treatment of Cancer, Neurological and Tissue Degenerative Diseases

Elucidation of the genes involved in cellular proliferation and the underlying mechanisms that promote and inhibit cell cycle progression has required the use of simple, genetically manipulable model systems. Baker's yeast *Saccharomyces cerevisiae* and fission yeast *Schizosaccharomyces pombe* are single celled eukaryotes which have been used extensively as model organisms for basic mechanistic investigations into how cells grow and divide, as well as for rapid, target-based screening of potential growth-regulating therapeutic compounds. The attractiveness of using these model systems includes facile manipulations of yeast genes, availability of the complete genomic sequence of baker's yeast, and identification of numerous yeast genes which directly correlate with known human disease genes. One fundamental discovery that has become clear from the use of these model systems is that many critical regulatory pathways and the proteins which control cell growth and division are highly conserved among all eukaryotes. Importantly, mammalian homologues of many yeast proteins known to be important in regulating cell proliferation, including the cyclin-dependent kinases, cyclins and basal transcription machinery can functionally substitute for the yeast proteins. Therefore these model systems have been effectively utilized for the rapid identification and functional characterization of mammalian homologues of conserved genes and understanding the mechanisms and cellular targets of drugs that interfere with conserved signal transduction cascades. Thus yeast is a very attractive model system not only for the elucidation of basic cell biology but also for large-scale screening of compounds which specifically target cell growth in a well-defined genetic background.

The present invention pertains to substantially purified novel genes (Emg1, Emg1-1 and ENIP1) and to compounds and methods for the screening of agonists and antagonists that modulate the activity of the genes or the translation products of the genes. The identification of such compounds will be beneficial in the treatment of, e.g., various cancers. The present invention is not limited to the identification of compounds for the treatment of a particular cancer. The identification of compounds for the treatment of many various cancers is contemplated. Additionally, the present invention contemplates the identification of compounds that will be useful in the treatment of diseases where the initiation of mitosis will be beneficial. The invention is not limited to the identification of compounds for the treatment of a particular disease by stimulating mitosis. Treatments for many various diseases are contemplated, e.g., various neurological diseases, such as Alzheimers or Parkinson disease, and various tissue degenerative diseases, such as cirrhosis of the liver.

B. Treatment of Fungal Diseases

Fungi are single celled living forms of life which inhabit the land, air and waters of the earth. They are more highly developed than bacteria and viruses. It is estimated that there are over 500,000 different species. Fungi have existed on earth hundreds of millions of years and, quite remarkably, have experienced little genetic change during that period of time. Viable fungi can grow from spores which have been dormant for thousands of years, such as has been observed in spores which were found in Egyptian tombs.

Single fungal cells can only be seen under the microscope, but a colony of these cells makes a visible presence in the form of mushrooms, toad stools and molds on food or elsewhere. While plants, animals and humans are alive and well, the fungi around them are usually unable to overcome the natural defense mechanisms which higher forms of life possess. Once death of the living organism has occurred, however, the fungi become the principle undertakers and managers. They are instrumental in reducing all that has ever lived into the molecules from which they were assembled.

Unfortunately, though, there is one exception to this simple balanced equation of life and death and that is that the fungi can also attack living cells. At its most simplistic perspective, one has many fungi entering the intestinal tract, the nose and lungs, and organs exposed to the outside world. Though we generally do not develop an infection from such intrusions, some persons might contract a fungal infection such as "athlete's foot" or "ring worm" on the skin.

At the opposite extreme is the patient with AIDS who faces major life-threatening fungal infections because the immune system has lost its ability to protect the body from organisms which invade the body, such as fungi. In between these extremes are fungal infections associated with diseases such as diabetes, cancer as well as conditions which include intra- and inter-specific cross infections. Two groups of fungi that are of medical importance are yeast and molds. Both are nearly ubiquitous and species of both can cause infections in mammals. Common ailments attributed to fungi are yeast infections and various fungal skin infections. More severe medical conditions can occur if internal infections arise, e.g., after surgery. Additionally, fungi produce mycotoxins. Mycotoxins are biologically active substances that have evolved as a protective mechanism for the fungus. Some mycotoxins have become useful to humans. Antibiotics, such as penicillin, are examples. However, many mycotoxins can be harmful or deadly. Fungal infections, therefore, are not only limited to the site of infection, but, through the production of mycotoxins, can adversely affect the entire organism. For example, mycotoxins have been linked to cancer. Therefore, even if the fungal infection is cleared, the patient may still suffer long term consequences as a result of the infection.

This invention contemplates the screening of compounds that can be useful as anti-fungal agents. To be useful as an anti-fungal therapeutic, the desired compound would have to be toxic to the fungus without causing undue negative effects on the patient. The invention, by virtue of utilizing both the yeast gene and the human homolog, provides a screen where compounds specific for yeast (and with no or little impact on human cells) can be identified.

DETAILED DESCRIPTION OF PREFERRED EMBODIMENTS

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y., which are incorporated herein by reference) which are provided throughout this document. All the information contained therein is incorporated herein by reference.

Oligonucleotides can be synthesized on an Applied BioSystems oligonucleotide synthesizer [for details see Sinha et al., Nucleic Acids Res. 12:4539 (1984)], according to specifications provided by the manufacturer. Complementary oligonucleotides are annealed by heating them to 90° C. in a solution of 10 mM Tris-HCl buffer (pH 8.0) containing NaCl (200 mM) and then allowing them to cool slowly to room temperature. For binding and turnover assays, duplex DNA is purified from native polyacrylamide (15% w/v) gels. The band corresponding to double-stranded DNA is excised and soaked overnight in 0.30 M sodium acetate buffer (pH 5.0) containing EDTA (1 mM). After soaking, the supernatant is extracted with phenol/chloroform (1/1 v/v) and precipitated with ethanol. DNA substrates are radiolabeled on their 5'-OH group by treatment with [g-$^{32}$P]ATP and T4 polynucleotide kinase. Salts and unincorporated nucleotides are removed by chromatography on Sephadex G columns.

Assays for detecting the ability of agents to inhibit or enhance Emg1-mediated and ENIP1-mediated mitosis provide for facile high-throughput screening of agent banks (e.g., compound libraries, peptide libraries, and the like) to identify antagonists or agonists. Such Emg1 pathway antagonists and agonists may be further developed as potential therapeutics and diagnostic or prognostic tools for diverse types of cancers, neurological diseases and in tissue repair. Likewise, the Emg1, Emg1-1 and ENIP1 genes, and modifications thereof, may be useful in gene therapy. For example, the incorporation of the Emg1, Emg1-1 or ENIP1 gene sequence into cells in context of tissue specific or inducible promoters might be useful in the treatment of hereditary diseases.

1. Screens to Identify Agonists of Antagonists of Emg1, Emg1-1 and ENIP1 Activity There are several different approaches contemplated by the present invention to look for small molecules that specifically inhibit or enhance the activity of Emg1, Emg1-1 or ENIP1. One approach is to transfect expression constructs (vectors) comprising the Emg1, Emg1-1 or ENIP1 gene (e.g., human gene) into cells and measure changes in the rate of mitosis as compared to controls after the cells have been exposed to the compound suspected of modulating Emg1, , Emg1-1 or ENIP1 activity. Cells may be transiently transfected or stably transfected with the construct under control of an inducible or temperature sensitive promoter. Other embodiments would include translation of the invention and purification of the peptide. The purified peptide could then be used as a substrate in a cell-free assay. Furthermore, transgenic animals and temperature sensitive yeast cell lines could be produced allowing for in vivo assays to be conducted.

A. In vitro Assays i. Transfection Assays

Transfection assays allow for a great deal of flexibility in assay development. The wide range of commercially available transfection vectors will permit the expression of the invention in a extensive number of cell types. Additionally, Emg1 and ENIP1 have been shown to regulate mitosis in a number of yeast cell types and in mammalian cells. In one embodiment, cells are transiently transfected with an expression construct comprising, in operable combination, a mutated (lof) Emg1 gene and an inducible promotor allowing for the initiation of translation and transcription when needed. Cells are exposed to the agent suspected of modulating Emg1 activity, Emg1 expression is initiated and mitosis is measured. Rates of mitosis in cells expressing the mutant are compared to rates of mitosis in cells transfected with a construct expressing a wild type Emg1 gene and cells expressing an empty expression vector (i.e., a control). Rates of mitosis are quantitated by any of a number of ways reported in the literature and known to those practiced in the art. The present invention also contemplates the use of the Emg1-1 and ENIP1 genes in the preceding embodiments.

In another embodiment, stably transfected cells lines are employed. The use of an inducible promoter or temperature sensitive promoter can be utilized in these systems. Screening assays for compounds suspected of modulating Emg1, Emg1-1 or ENIP1 activity are conducted in the same manner as with the transient transfection assays. Using stably transfected cell lines, however, allows for greater consistency between experiments and allow for inter-experimental comparisons.

B. In Vivo Assays i. Transgenic Animal Assays

In one embodiment, transgenic animals are constructed using standard protocols, including homologous recombination. The generation of transgenic animals will allow for the investigation of diseases for which the mutated forms of Emg1, Emg1-1 or ENIP1 may provide the means for determining the physiology of the disease or its treatment.

ii. Yeast Based Assays

In one embodiment, transgenic yeast are constructed using standard protocols, including homologous recombination. The generation of transgenic yeast will allow for the investigation of diseases for which the mutated forms of Emg1, Emg1-1 or ENIP1 may provide the means for determining the physiology of the disease or its treatment. Mutant yeast may be constructed by using mutant Emg1, Emg1-1 or ENIP1 genes such as lof or gof mutants.

2. Screens to Identify Emg1 Signal Pathway Constituents

A. In vitro Assays

There are several different approaches to identifying Emg1 interactive molecules or binding partners. Techniques that may be used are, but not limited to, immunoprecipitation of Emg1 with antibodies generated to the translation product of the invention. This would also bring down any associated bound proteins, i.e., proteins in the cell with affinity for the Emg1 polypeptide. Another method is to generate fusion proteins containing the mutant form of Emg1 connected to a generally recognized pull-down protein such as glutathione S-transferase (GST). Bound proteins can then be eluted and analyzed. Yet another method is to bind Emg1 to a solid support and expose the bound Emg1 to cell extracts suspected of containing an Emg1 interactive molecule or binding partner. ENIP1 is an example of an Emg1 interacting molecule. Those practiced in the art will recognized that variations of these approaches may be used to identify ENIP1 interacting proteins.

i. Immunoprecipitation

After the generation of antibodies to wild type and mutant (e.g., Emg1-1) Emg1, cells expressing transfected Emg1 are lysed and then incubated with one of the antibodies. Antibodies interact with the bound Emg1 and any associated proteins can then be pulled down with protein-A Sepharose or protein-G Sepharose beads, using standard techniques. Where yeast binding partners are sought, yeast cells are lysed. Where human binding partners are sought, human cells are lysed and the human Emg1 gene is used.

ii. Fusion Protein Pull-down

A method similar to immunoprecipitation is to construct fusion proteins of the mutant and wild type Emg1, Emg1-1 or ENIP1 and glutathione S-transferase (GST). The GST fusion proteins are then incubated with cell extracts and then removed with glutathione Sepharose beads. Any bound, Emg1-, Emg1-1- or ENIP1-associated proteins are then characterized.

B. In Vivo Assays i. Yeast Two-hybrid System

The yeast two-hybrid system that identifies the interaction between two proteins by reconstructing active transcription factor dimers. The dimers are formed between two fusion proteins, one of which contains a DNA-binding domain (DB) fused to the first protein of interest (DB-X, where X will be Emg1) and the other, an activation domain (AD) fused to the second protein of interest (AD-Y, where Y will be a protein encoded by cDNA from a commercially available library). The DB-X:AD-Y interaction reconstitutes a functional transcription factor that activates chromosomally-integrated reporter genes driven by promoters containing the relevant DB binding sites. Large cDNA libraries can be easily screened with the yeast-two hybrid system. Yeast cDNA libraries are commercially available. Standard molecular biological techniques can be employed to isolate and characterize the interacting protein.

3. Screens to Identify Emg1, Emg1-1 and ENIP1 Homologs

Standard molecular biological techniques can be used along with the reagents of the present invention to identify Emg1, Emg1-1 or ENIP1 homologs in various species. For example, preferred embodiments may included, but are not limited to, DNA-DNA hybridization techniques (e.g., Southern blots) and DNA-RNA hybridization techniques (e.g., Northern blots). Additional techniques may include, for example, immunoscreening of proteins made from library stocks by antibodies generated from the invention. The present invention also contemplates a number of approaches including, but not limited to, immunoprecipitation and affinity purification of cell and tissue extracts and immunoscreening of proteins and glycoproteins translated from DNA and RNA library stocks. Furthermore, hybridization screens of RNA and DNA library stocks could be accomplished using RNA and DNA sequences reverse engineered from isolated Emg1 protein.

EXPERIMENTAL

The following examples are intended to illustrate, but not limit, the present invention. Additionally, the following examples employ standard molecular biological, microbiological and cell culture procedures. These techniques and procedures are generally performed according to conventional methods in the art (see, generally, Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y., which are incorporated herein by reference).

EXAMPLE I
Identification, Isolation and Characterization of Emg1

In this example, a novel gene in the budding yeast Saccharomyces cerevisiae called Essential for Mitotic Growth 1 (Emg1) which encodes a protein of 252 amino acids was identified, isolated, and characterized. The sequence of this protein is unique within the S. cerevisiae genome. Computer-aided searches of known databases for homologous genes in other organisms has revealed the presence of highly similar genes in fission yeast, worm, rice, mouse and humans suggesting that the structure and potential function of the Emg1 protein is evolutionarily conserved. Except for these highly similar homologues, this protein does not align with any significant homology to any other described or sequenced protein or characterized protein functional domain. The lack of similarity suggests that this protein may define a new class of protein with an unique cellular function.

To understand the function of the Emg1 protein, S. cerevisiae cells, denoted strain PLY12, were created in which the Emg1 gene has been insertionally inactivated by homologous recombination. S. cerevisiae cells lacking the Emg1 gene are not viable demonstrating that the Emg1 gene is essential for cell proliferation (FIG. 1). Briefly, in FIG. 1, diploid wild type yeast (Emg1/Emg1) or heterozygous diploid cells in which one copy of the Emg1 gene had been insertionally inactivated by homologous recombination (Emg1/emg1Δ) were sporulated and the meiotic progeny dissected by micromanipulation. Shown are the results for four independent tetrads (1–4) and the four spore clones per tetrad (A–D). Microscopic inspection revealed that spores germinating from emg1Δ cells underwent 2–3 rounds of cells division before terminating growth. Furthermore, we have demonstrated that the Emg1 gene is not required for the germination of S. cerevisiae spores, the products of meiosis, but rather Emg1 is essential for mitotic proliferation. The Emg1 gene and protein are highly expressed during conditions of normal growth. In response to a variety of cellular stress such as elevated temperatures, toxic levels of heavy metals, oxidants or ethanol, the levels of Emg1 mRNA are rapidly, dramatically and transiently diminished. During periods of stress which can lead to damage to multiple cellular targets including proteins, nucleic acids and membranes, cells temporarily cease cell division by downregulating or inactivating the genes and proteins that promote proliferation and activate programs of cellular defense and repair until homeostatic conditions are restored. The exquisite sensitivity of the Emg1 mRNA to stress and its rapid restoration upon cell recovery is similar to the pattern of mRNA expression for other critical regulators of cell growth, further supporting the observation that Emg1 protein is essential for cell proliferation. This is also supported by our observation that the levels of Emg1 protein which are easily detectable under conditions of rapid cell growth become very low when cells stop growing as they enter into stationary phase. Thus we have identified a novel yeast protein, Emg1, which is abundantly expressed in rapidly proliferating cells and is essential for yeast cell mitotic growth.

Figure 3:
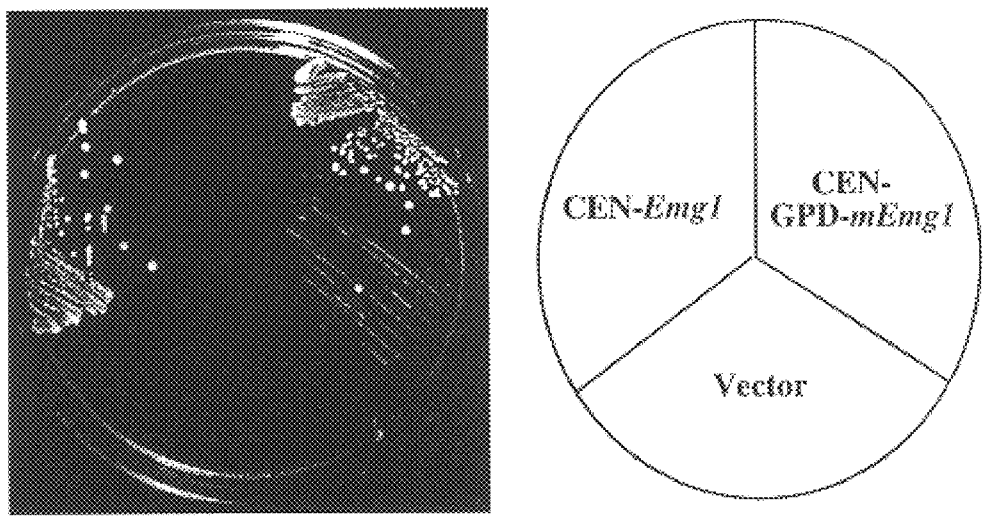
FIG. 3 shows mouse Emg1 corrects the viability of defect of PLY12 cells.
Figure 4A:
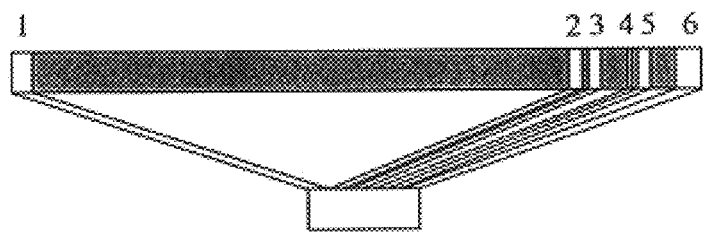
FIG. 4, panels A and B show the characterization of mouse Emg1. In particular, FIG. 4, panel A, depicts the genomic structure of mEmg1 showing the exons encoding the Emg1 c DNA (white boxes) and intervening introns (stippled boxes).
Figure 4B:
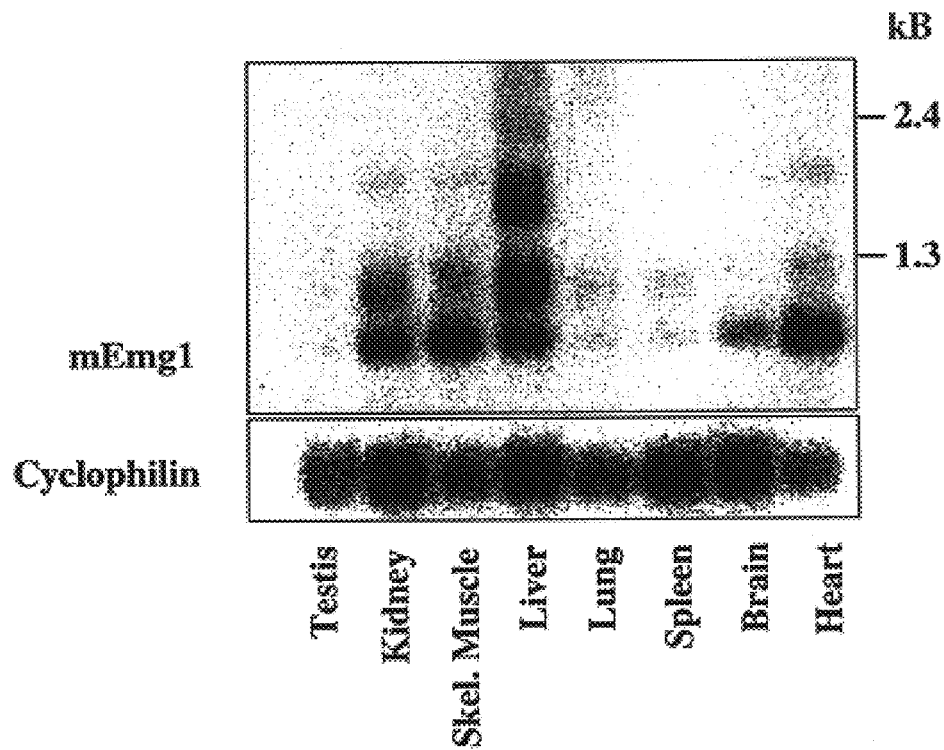

Our identification of the S. cerevisiae Emg1 gene as a stress-responsive gene that is essential for mitotic cell growth prompted us to ascertain whether there exist structurally and functionally homologous counterparts in mammals. A detailed computer-aided analysis of expressed sequenced tagged (EST) databases revealed the existence of complementary DNA sequences from the worm, C. elegans, mouse and humans encoding proteins with approximately 50% identity to the S. cerevisiae Emg1 protein (FIG. 2). No reports on the sequences of the C. elegans, mouse or human complementary DNAs, encoded proteins or their functions have been published at the current time. To ascertain if the cDNAs from mammals encode proteins with functional similarity to the S. cerevisiae Emg1 protein, functional complementation studies were carried out in yeast cells. A yeast strain designated PLY12, containing a deletion of the chromosomal Emg1 gene and a wild type Emg1 gene on a single copy URA3-based plasmid, was transformed with a yeast expression plasmid in which the mouse Emg1 cDNA is expressed from the GPD (Glycerol Phosphate Dehydrogenase) promoter. The loss of the plasmid borne yeast Emg1 gene was selected by growth of cells on 5-Fluororotic acid (5-FOA) containing solid medium and cultures inspected for the presence of viable cells lacking the S. cerevisiae emg1 gene but containing the mouse Emg1 expression plasmid. The results of these experiments demonstrated that expression of the mouse cDNA, encoding a protein with structural similarity to the S. cerevisiae Emg1 protein, is able to replace the yeast Emg1 protein in its essential role in mitotic cell growth (FIG. 3). Briefly, in FIG. 3 a plasmid harboring the yeast Glycerol Phosphate Dehydrogenase promoter was used to express yeast Emg1 (CEN-Emg1), the mouse Emg1 cDNA (CEN-GPDmEmg1), or vector alone (Vector) and transformed into yeast strain PLY12. Cell viability was assessed by streaking transformants onto 5-Fluororotic acid medium. Furthermore, these data suggest that the mammalian Emg1 proteins play an important role in cell proliferation in mammalian cells. It is important to note that the mouse Emg1 messenger RNA (mRNA) is expressed in a number of distinct mouse tissues (FIG. 4). In particular, FIG. 4, panel A, depicts the genomic structure of mEmg1 showing the exons encoding the Emg1 c DNA (white boxes) and intervening introns (stippled boxes). FIG. 4, panel B depicts a blot analysis of the distribution of Emg1 mRNA in mouse tissues.

EXAMPLE 2
Identification and Isolation of Emg1 Structural and Functional Homologues In this example, we investigate a number of feasible strategies for the identification and isolation of complementary DNAs from other organisms, such as plants, pathogenic fungi, cattle and so forth, encoding proteins that are functionally homologous to the S. cerevisiae Emg1 protein. These approaches include: 1) the use of DNA sequence database searches to identify cDNAs encoding Emg1 homologues 2) the use of the S. cerevisiae, worm, mouse, human or other existing genes or cDNAs encoding Emg1 as probes in hybridization assays to identify homologous DNA fragments 3) the use of complementation in Emg1Δ yeast cells by the introduction of complementary DNA libraries under the control of DNA sequences that drive expression of the cDNAs in yeast cells. 4) The use of degenerate oligonucleotides as radioactive hybridization probes or in polymerase chain reactions to identify genomic DNA or cDNA fragments encoding Emg1 proteins. 5) The use of anti-Emg1 polyclonal anti-serum to screen expression libraries for cDNAs encoding Emg1-like proteins.

EXAMPLE 3

Screens for Compounds that are Antagonistic or Agonistic to Proliferation

In this example, we investigate the use of Emg1 and derivative products as reagents to screen for anti-proliferative and pro-proliferative agents. Emg1 protein is essential for mitotic cell growth in yeast cells. Given the sequence similarity and functional complementation by mammalian Emg1 proteins it is likely that Emg1 is also of general importance in cellular proliferation in mammals, including humans, and is therefore a target for the action of molecules that modify cell proliferation. Such molecules will include antibodies, chemicals, RNA aptamers and other small molecules that neutralize, antagonize or promote the activity of Emg1. Additionally, such molecules might interfere with or enhance the interactions between Emg1 protein and other cellular molecules essential for Emg1 protein action in cell cycle progression. In one such assay, yeast cells are transfected with vectors encoding human Emg1, yeast Emg1 or a temperature sensitive lof mutant yeast Emg1. Suspected proliferative modifying agents are then put into contact with the transfected yeast cells and the cells are raised to the restrictive temperature. Agents that promote proliferation will overcome the effect of the Emg1 lof mutant. Agents that inhibit proliferation will inhibit cell growth in the cultures transfected with the human Emg1 gene. The cells transfected with the yeast Emg1 gene will serve as a control for the lof mutant and the cells expressing the human homolog. This assay, and modifications thereof, screen for the ability of suspected compounds to be either agonistic or antagonistic to proliferation. The identification of such proliferation antagonists might prove beneficial to the treatment of diseases including, but not limited to, cancers. The identification of proliferation agonists might prove beneficial to the treatment of diseases such as Alzheimer's and Parkinson's disease, other tissue degenerative diseases and tissue regeneration procedures.

EXAMPLE 4

Emg1 as an Stimulator of Cell Proliferation

In this example, we investigate the use of Emg1 as an enhancer of cell proliferation. In this example cells are removed from a patient and transfected with a vector encoding Emg1. The cells, or a portion thereof, are then reintroduced into the patient. These cells would be enhanced for the ability to proliferate. Once returned to the patient they might be instrumental in the rebuilding of diseased or destroyed tissues. One anticipated medical condition that is a candidate for such treatment would be, for example, cirrhosis of the liver. Additionally we investigate the generation of small peptides or other molecules that biologically mimic the Emg1 active site or domain may be used to stimulate cell proliferation. The identification of binding partners in eukaryotic cells that are essential for Emg1 action will provide the basis for the discovery of Emg1 agonists.

EXAMPLE 5

Emg1 as a Target for Anti-fungal Agents

In this example, we investigate the use of Emg1 and derivative products for the identification of anti-fungal products. The requirement for Emg1 in yeast cell growth suggests that regions of Emg1 are unique to yeast or other pathogens and not present in mammals. These areas will be used as a target for the generation of pharmacologic agents used as anti-fungal agents or to combat other infectious eukaryotic organisms. Assays are performed in vivo and in vitro. Emg1 will be coupled to an appropriate resin for use in a chromatography column. The compounds suspected of binding to Emg1 will be run through the column and, after washing away unbound or nonspecifically bound molecules, such compounds will be eluted and characterized. Molecules isolated from cell lysates may be in vivo binding partners to Emg1. Blotting experiments will confirm the results of the chromatography experiments. Molecules isolated from libraries of molecular compounds might function as agonists or antagonists to Emg1 in vivo activity. Transfection assays, as presented above, will permit the identification of those molecules with activity agonistic or antagonistic to Emg1 function. Compounds antagonistic to Emg1 will be screened for therapeutic activity against known species of fungi that infect animals (including humans) or plants.

EXAMPLE 6

Assays for the use of Emg1 Genes, cDNAs and Proteins

1. Assays in Yeast Cells

In this example, we investigate the use of yeast cells bearing a deletion of the endogenous Emg1 gene as recipients for the expression of Emg1 encoding cDNAs or genes for the identification and analysis of effectors of Emg1 activity or molecules that stimulate or inhibit the interaction of Emg1 protein with partner proteins. This will be evaluated by using the two-hybrid protein-protein interaction assay.

2. Assays in vitro

In this example, we investigate whether the use of purified Emg1 protein from various sources could be used for the identification and analysis of effectors of Emg1 activity in vitro. For example, inhibitors of any catalytic activity that Emg1 protein possesses will be tested in vitro. Secondly, molecules that inhibit or stimulate interactions between Emg1 and partner proteins will be analyzed in vitro by biochemical fractionation experiments to evaluate the presence of Emg1-partner protein complexes by column chromatography, electrophoresis or fluorescence energy transfer analysis.

3. Assays in Cultured Mammalian or Insect Cells

In this example we investigate whether mammalian or insect cells expressing Emg1 cDNAs or genes could be used for the identification and analysis of effectors of Emg1 activity and for the identification of the factors that functionally interact with Emg1. For example, the effects of Emg1 on cell proliferation will be measured by transfecting Emg1 protein expressed from Emg1 cDNAs under the control of the CMV promoter in the plasmid pCDNA (marketed by InVitrogen). Cell proliferation will be measured by a number of assays including radiolabeled thymidine incorporation, trypan blue exclusion for viability or ELISA-based enzymatic assays for cell proliferation.

EXAMPLE 7

Isolation and Characterization of a Temperature Sensitive Allele of EMG1

Figure 10A:
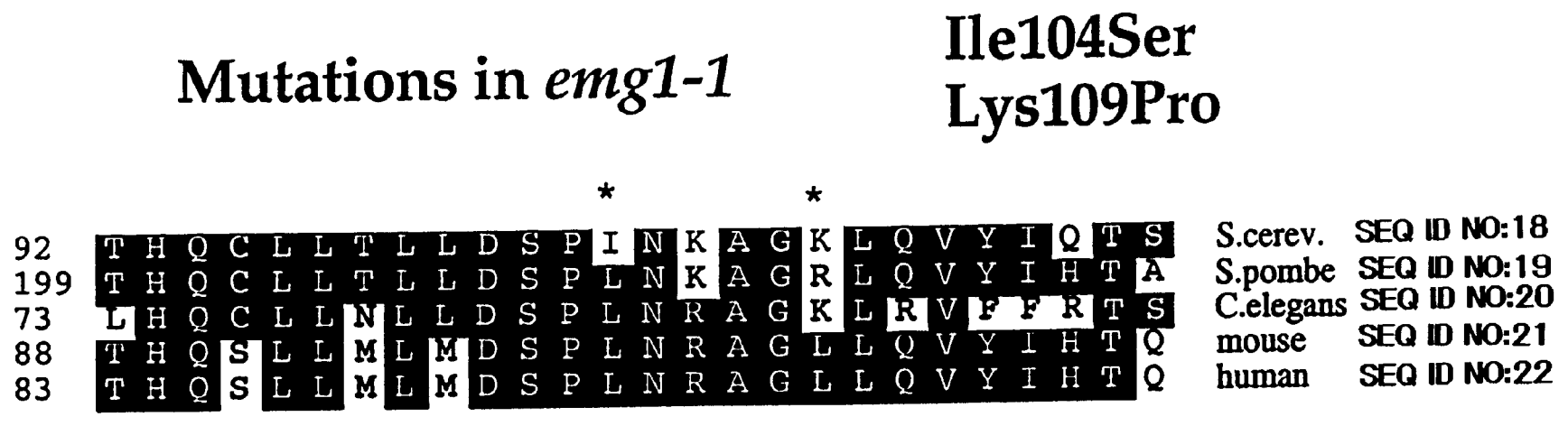
Figure 10B:
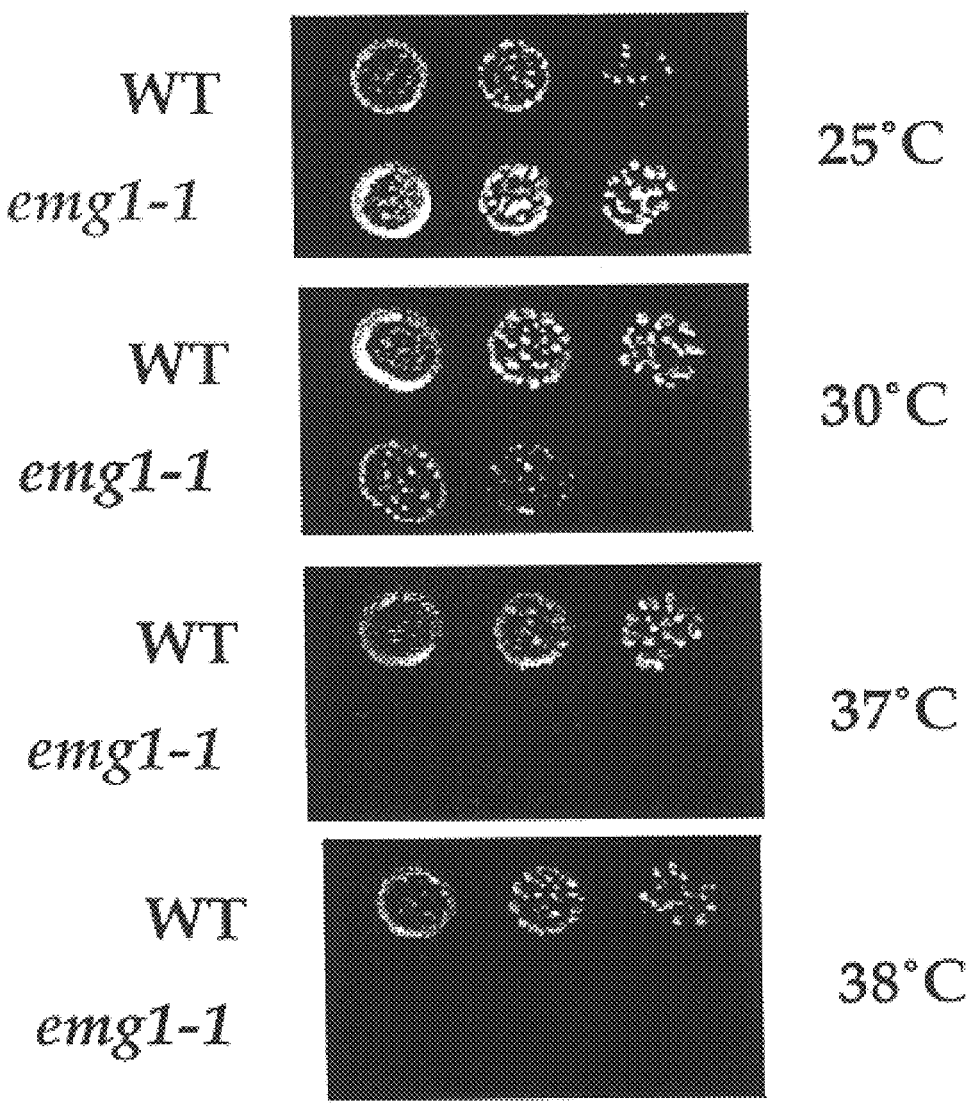
FIG. 10B shows the temperature sensitive growth inhibition of Emg1-1.

A loss of function (lof) mutant of Emg1, designated Emg1-1, has been isolated which harbors 2 point mutations within the open reading frame, Ile104Ser and Lys109Pro (FIG 10A, asterisks indicate point mutations). These mutations lie within a region of the protein that is highly conserved among all known Emg1 sequences and identify an important domain of Emg1 that is critical for proper regulation of cell growth. Although the mutant protein appears to function normally at low temperatures (25°) based on cell growth assays, cells harboring the emg1-1 allele grow slowly at slightly higher temperatures (30°) compared to wild-type cells and completely arrest growth at elevated temperatures (37° and 38°) (FIG. 10B). Wild-type and emg1-1 mutant cells were diluted serially, spotted on to agar plates and incubated at the indicated temperatures for 3 days. This experiment demonstrates the sensitivity of the mutant cells to elevated temperatures for growth. These data indicate that proper function of Emg1 is absolutely required for cell proliferation and that specific mutations or compounds that disrupt Emg1 protein function will likely inhibit cell growth.

EXAMPLE 8
Emg1 is a Nuclear Protein

Figure 11:
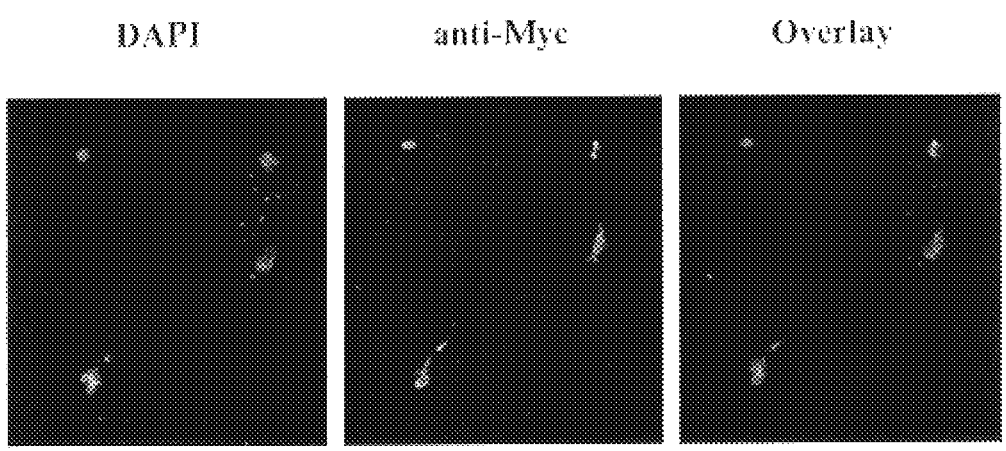
FIG. 11 shows by immunofluorescence that Emg1 is a nuclear protein.

Emg1 has been clearly identified an a resident nuclear protein under normal growth conditions by conventional immunocytological techniques. The signal from a myc epitope tagged-copy of Emg1 (Emg1p) largely overlaps with the DAPI-stained chromosomal DNA from signal in the nucleus. Yeast expressing a functional myc epitope tagged allele Emg1 were stained with DAPI to visualize the location of the cell nucleus (FIG. 11, left panel, blue staining) and then subjected to indirect immunofluorescence using an anti-MYC antibody to visualize Emg1p (FIG. 11, center panel, red staining). An overlay of the two images (FIG 11, right panel, purple staining) shows coincident signals from DAPI and myc-Emg1p indicating that Emg1 is present in the cell nucleus.

EXAMPLE 9
Identification of an Emg1-Interacting Protein (ENIP1)

Figure 15A:
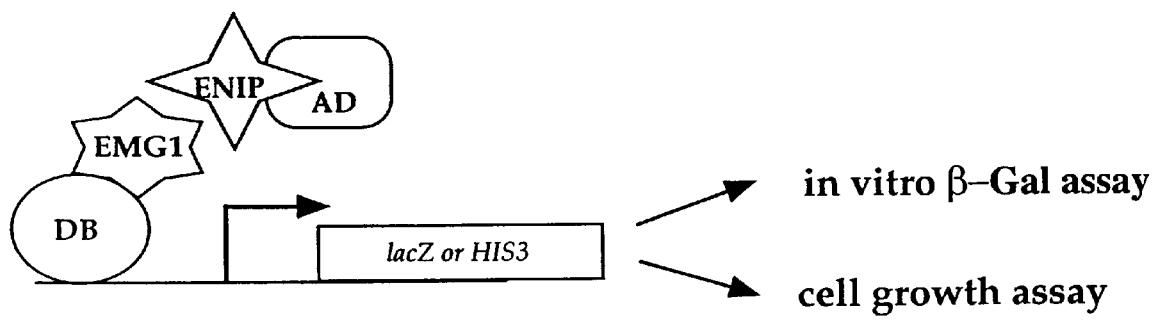
FIG. 15A shows the methodology used in the two-hybrid screen used to show Emg1/ENIP1 interaction.
Figure 15B:
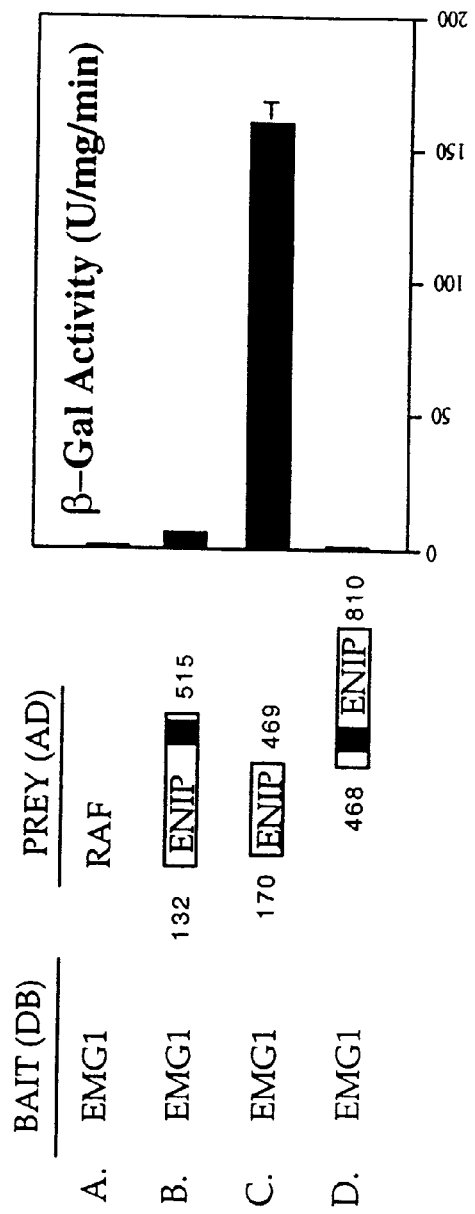
FIG. 15B shows mapping of the Emg1 binding domain of ENIP1 to a region between amino acid 170 and 469 (row C).
Figure 15C:
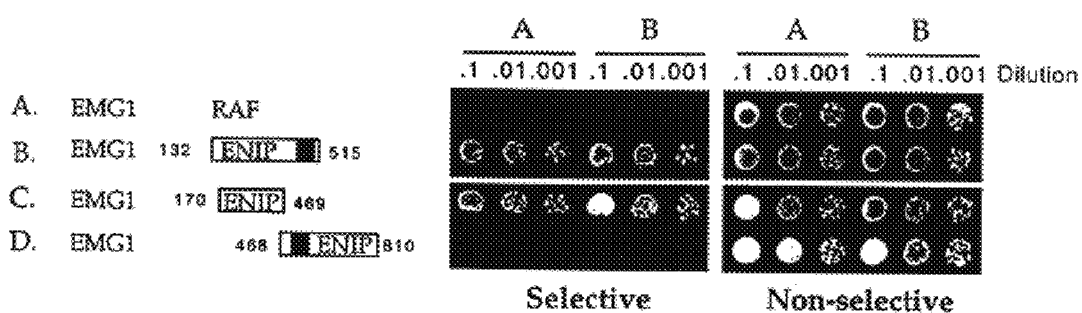
FIG. 15C shows a cell growth assay on selective medium (no histidine) to confirm interaction between Emg1 and ENIP1.

A yeast protein was isolated that interacts with Emg1 which we have designated Emg1-Nuclear Interacting Protein 1 (ENIP1) using a yeast two-hybrid screen (FIGS. 15A and 15B). The ENIP1 gene (SEQ ID NO:24) (*S. cerevisiae* gene locus YDL148c) encodes a protein of 810 amino acids (SEQ ID NO:25) with limited homology to other yeast proteins based on computer-aided sequence comparisons. Searches of sequence databases from other organisms have revealed the presence of similar amino acid sequences in fission yeast (SEQ ID NO:26), worm (SEQ ID NO:27) and humans (SEQ ID NO:28) coding for proteins of 827, 848 and 873 residues, respectively. Pairwise analysis between the yeast and human amino acid sequences indicate approximately 25% sequence identity over the entire length of the protein (FIGS. 14A and 14B). The yeast ENIP1 has been shown to co-purify with proteins forming the nuclear pore complex (Rout, et al. "The yeast nuclear pore complex: Composition, architecture and transport mechanism" *J Cell Biol* 148:635–651, 2000).

Figure 18:
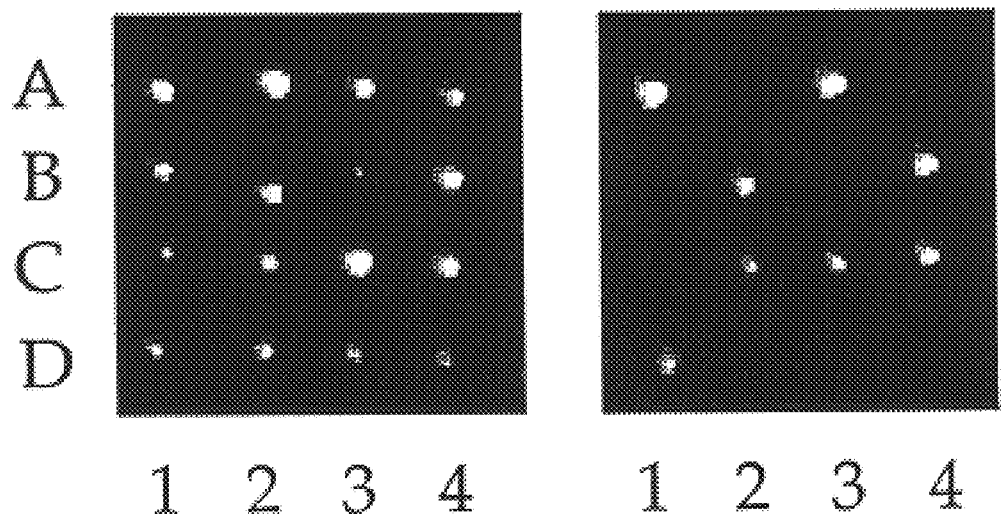
FIG. 18 shows that ENIP1 is essential for yeast growth.

FIG. 18 shows that the yeast ENIP1 gene it is essential for cell growth. Diploid wild-type yeast (ENIP1/ENIP1) or heterozygous diploid cells in which one copy of the ENIP1 gene had been insertionally inactivated by homologous recombination (ENIP1/enip1Δ) were sporulated and the meiotic progeny dissected by micromanipulation. Shown are the results for four independent tetrads (1–4) and the four spore clones per tetrad (A–D).

EXAMPLE 10
Emg1 and ENIP1 Physically Associate in vivo

Figure 16:
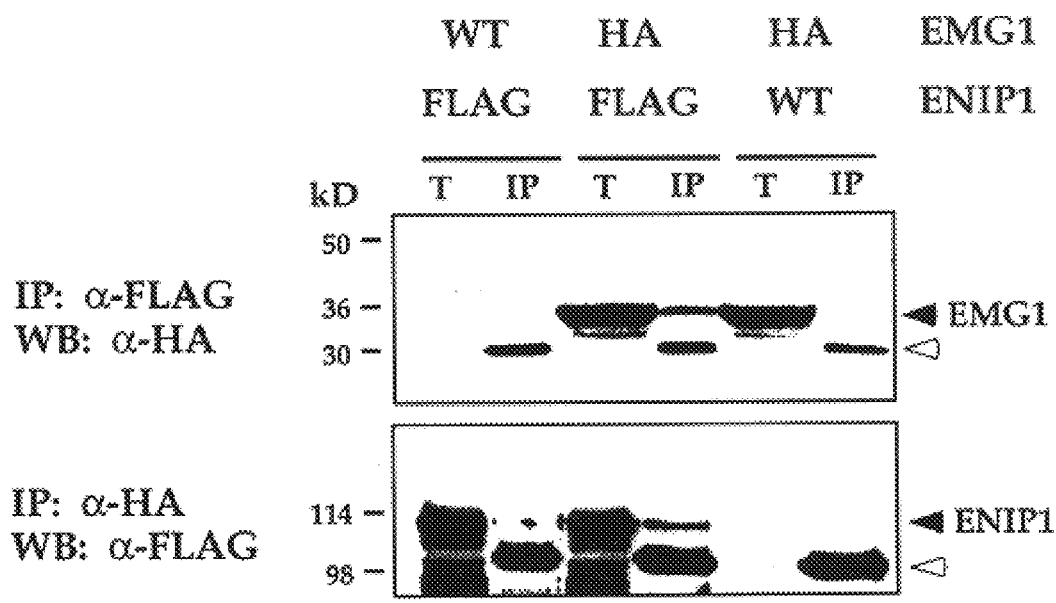
FIG. 16 shows a co-immunoprecipitation assay that demonstrates Emg1 and ENIP1 physically associate in vivo.

The interaction between Emg1 and ENIP1 has been characterized using in vivo assays as well as methods to detect in vivo interactions. Using the yeast two-hybrid system, we have mapped the domains of ENIP1 that are essential for the interaction with Emg1. By construction of a series of truncation deletions, we have identified that a central region of the ENIP1 protein from amino acids 170 to 470 are critical for modulating its binding to Emg1 as measured by in vitro enzymatic assays using β-galactosidase or by cell growth assays on medium lacking histidine. The binding between Emg1 and ENIP1 is robust. These proteins can be detected together in a complex in vitro by co-immunoprecipitation. FIG. 16 shows that a stable complex between Emg1 and ENIP1 is detected in the antibody pull-down assays only in the middle lanes of each panel where Emg1 and ENIP1 have been tagged with HA and FLAG, respectively, demonstrating the specificity of the experimental protocol. In FIG. 16, the lanes labeled "T" are total cell extract and the lane labeled "IP" are immunoprecipitated samples. Also in FIG. 16, black arrowheads indicate Emg1 or ENIP1 detection and white arrowheads indicate free IgG. In addition, binding between Emg1 homologs and ENIP1 homologs is very likely to be conserved because we have successfully detected a strong interaction between the mouse Emg1 protein and the yeast ENIP1 protein fragment (composed of amino acids 170–469) that interacts with yeast Emg1. Therefore, the binding between ENIP1 and Emg1 appears to be an important interaction for regulating or facilitating the role of yeast Emg1 in mitotic growth and suggests that this complex will also be important in mammalian cell proliferation. Finally, we have demonstrated that deletion of the ENIP1 gene, like Emg1, leads to an inability of yeast cells to proliferate. Given that Emg1 and ENIP1 are both essential genes and that the interaction is critical for the proper function of Emg1, agents that can disrupt this interaction will likely also inhibit cellular proliferation.

Figure 17:
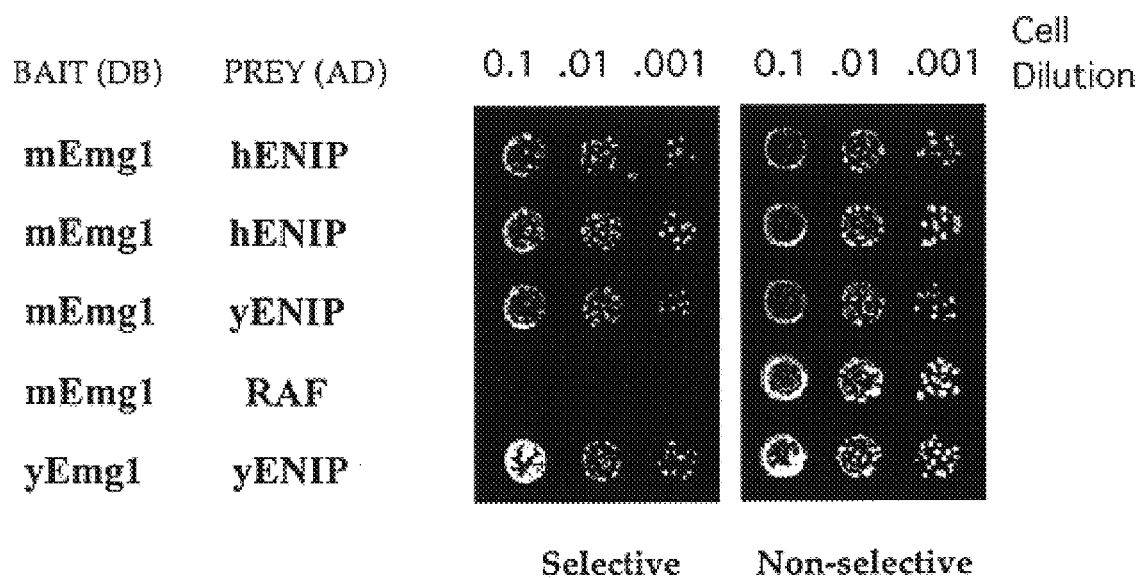
FIG. 17 shows by two-hybrid analysis that murine Emg1 interacts with human ENIP1.

FIG. 17 shows that mammalian Emg1 and ENIP1 proteins interact. Two-hybrid analysis of mouse-Emg1 (mEmg1 ) with human ENIP1 (hENIP) using a cell growth assay on selective (no histidine) or non-selective media confirms the interaction between these proteins. mEmg1 also interacts with the yeast ENIP1 (yENIP) demonstrating that the surfaces for interaction have been conserved through evolution but fails to interact with the human cRAF protein to indicate specificity of binding by Emg1 for ENIP1.

From the above it should be clear that the present invention provides a wide variety of ways to screen for compounds that can modulate Emg1 activity and, therefore, can regulate cellular mitosis. The means of identifying such compounds (now provided by the present invention) would permit the development of diagnostic and therapeutic procedures for the treatment of various cancers and neurological diseases as well as permit the development of anti-fungal treatments. Additionally, screens for Emg1 intra- and interspecific homologs as well as Emg1 associated binding molecules are possible as a result of this invention. Furthermore, this invention makes possible the construction of cells and organisms that are made deficient in expression of this gene or made to express additional copies of this gene.

What is claimed is:

1. A composition comprising isolated and purified DNA having an oligonucleotide sequence selected from the group consisting of SEQ ID NO: 10 and SEQ ID NO: 16.

2. A composition comprising purified RNA transcribed from the DNA of claim 1.

3. An expression construct comprising DNA of claim 1.

4. A method to detect Emg1 agonists and antagonists, comprising:
   a) providing: i) one or more compounds suspected of modulating Emg1 activity; ii) a first yeast cell line comprising the yeast Emg1 gene; and iii) a second yeast cell line transfected with the human Emg1 gene so as to create a transfected yeast cell line;
   b) contacting a portion of said cells from i) said first yeast cell line and ii) said transfected yeast cell line, with said one or more compounds under conditions such that said compound can enter said cells, so as to create treated portions and untreated portions of cells; and
   c) comparing the amount of cell division of said treated cells with the amount of cell division of said untreated cells.

* * * * *